(12) United States Patent
Yamaguchi

(10) Patent No.: US 6,646,325 B2
(45) Date of Patent: Nov. 11, 2003

(54) SEMICONDUCTOR DEVICE HAVING A STEP-LIKE SECTION ON THE BACK SIDE OF THE SUBSTRATE, AND METHOD FOR MANUFACTURING THE SAME

(75) Inventor: Tadashi Yamaguchi, Tokyo (JP)

(73) Assignee: Oki Electric Industry Co, Ltd., Tokyo (JP)

( * ) Notice: Subject to any disclaimer, the term of this patent is extended or adjusted under 35 U.S.C. 154(b) by 0 days.

(21) Appl. No.: 10/057,909

(22) Filed: Jan. 29, 2002

(65) Prior Publication Data

US 2003/0038367 A1 Feb. 27, 2003

(30) Foreign Application Priority Data

Aug. 21, 2001 (JP) ........................ 2001/250482

(51) Int. Cl.[7] ............................................. H01L 29/06
(52) U.S. Cl. ........................ 257/622; 257/618
(58) Field of Search .................. 257/594, 618, 257/619, 620, 622

(56) References Cited

U.S. PATENT DOCUMENTS

| 4,670,770 A | | 6/1987 | Tai .................... 357/60 |
| 5,019,943 A | | 5/1991 | Fassbender et al. ........ 361/396 |
| 5,037,782 A | * | 8/1991 | Nakamura et al. .......... 438/167 |
| RE34,893 E | * | 4/1995 | Fujii et al. .................. 257/419 |
| 5,514,898 A | * | 5/1996 | Hartauer .................... 257/417 |
| 5,591,665 A | * | 1/1997 | Bodensohn et al. ........ 438/268 |
| 5,825,076 A | * | 10/1998 | Kotvas et al. .............. 257/622 |
| 6,020,603 A | | 2/2000 | Tokunoh et al. ........... 257/171 |
| 6,049,124 A | | 4/2000 | Raiser et al. .............. 257/712 |
| 6,069,394 A | * | 5/2000 | Hashimoto et al. ........ 257/466 |
| 6,091,130 A | | 7/2000 | Oyamatsu et al. .......... 257/619 |
| 2001/0011772 A1 | | 8/2001 | Fukasawa et al. | |

FOREIGN PATENT DOCUMENTS

| JP | 05087949 | 11/1993 |
| JP | 06232255 A | 8/1994 |
| JP | 09063993 A | 3/1997 |
| JP | 09320911 A | 12/1997 |
| JP | 10308410 A | 11/1998 |
| JP | 11260974 A | 9/1999 |
| JP | 200103177 | 7/2001 |

* cited by examiner

Primary Examiner—Ngân V. Ngô
(74) Attorney, Agent, or Firm—Rabin & Berdo, P.C.

(57) ABSTRACT

A semiconductor device includes a semiconductor substrate having a first main surface having circuit elements formed thereon, a second main surface substantially opposite to the first main surface, and a plurality of side faces provided between the first main surface and the second main surface. The semiconductor device also includes a plurality of external terminals formed over the first main surface and respectively electrically connected to the circuit elements. The second main surface has a first steplike section which extends from a first side face of the plurality of side faces to a second side face opposite to the first side face.

55 Claims, 20 Drawing Sheets

SEMICONDUCTOR DEVICE HAVING A STEP-LIKE SECTION ON THE BACK SIDE OF THE SUBSTRATE, AND METHOD FOR MANUFACTURING THE SAME

BACKGROUND OF THE INVENTION

1. Field of the Invention

The present invention relates to a semiconductor device and a method for manufacturing the same. The present invention particularly relates to a semiconductor device having a semiconductor chip whose back is exposed, and a method for manufacturing the same.

This application is counterpart of Japanese patent application, Ser. No. 250482/2001, filed Aug. 21, 2001, the subject matter of which is incorporated herein by reference.

2. Description of the Related Art

With size reductions in portable devices, there has been a demand for a reduction in the size of semiconductor devices in the portable device. In order to meet such a demand, a semiconductor device called a "Chip Size Package" having outside dimensions approximately identical to those of a semiconductor chip has come along. As one form of the chip size package, there is known a semiconductor device called a "Wafer Level Chip Size Package" or "Wafer Level Chip Scale Package". In such a wafer level chip size package (hereinafter called "WCSP"), the surface of a semiconductor chip is sealed with a resin, whereas the back (silicon surface) thereof has an exposed structure. In the WCSP, an index mark such as a one pin mark or the like for determining the direction of mounting of the WCSP on a printed circuit board is formed on the back (silicon surface) of the exposed semiconductor chip by marking processing. As the marking processing, may be mentioned, for example, a laser mark system for forming each mark by laser processing.

However, the back (silicon surface) of the semiconductor chip is ground to further thin the thickness of the WCSP and due to reasons such as the difference between the linear expansion coefficient of silicon and that of the printed circuit board. The silicon surface thereof is held in a mirror state. A problem arises in that even if a laser is used to effect marking on the silicon surface held in such a mirror state, the difference between the intensity of light reflected by a location subjected to the marking and the intensity of light reflected by a location free of the marking is small, i.e., the contrast is low, and hence the recognition of each mark falls into difficulties. The difficulty of recognizing the mark means that the automatic mounting or packaging of the WCSP on the printed circuit board by use of an automatic mounting or packaging device provided with an image recognizer is also difficult. Further, the difficulty of recognizing the mark means that a visual inspecting device with an image recognizer encounters difficulties in determining whether the WCSP is placed in a proper orientation upon a visual inspection done after the packaging of the WCSP on the printed circuit board.

Thus there has been a demand for a semiconductor device capable of easily determining the direction of packaging.

SUMMARY OF THE INVENTION

It is an object of the present invention is to provide a semiconductor device that can easily determining the direction of packaging.

According to one aspect of the present invention, for achieving one or more of the above objects, there is provided a semiconductor device that includes a semiconductor substrate having a first main surface having circuit elements formed thereon, a second main surface substantially opposite to the first main surface, and a plurality of side faces provided between the first main surface and the second main surface. The semiconductor device also includes a plurality of external terminals formed over the first main surface and respectively electrically connected to the circuit elements. The second main surface has a first steplike section which extends from a first side face of the plurality of side faces to a second side face opposite to the first side face.

The above and further objects and novel features of the invention will more fully appear from the following detailed description, appended claims and the accompanying drawings.

DETAILED DESCRIPTION OF THE PREFERRED EMBODIMENTS

Figure 1:
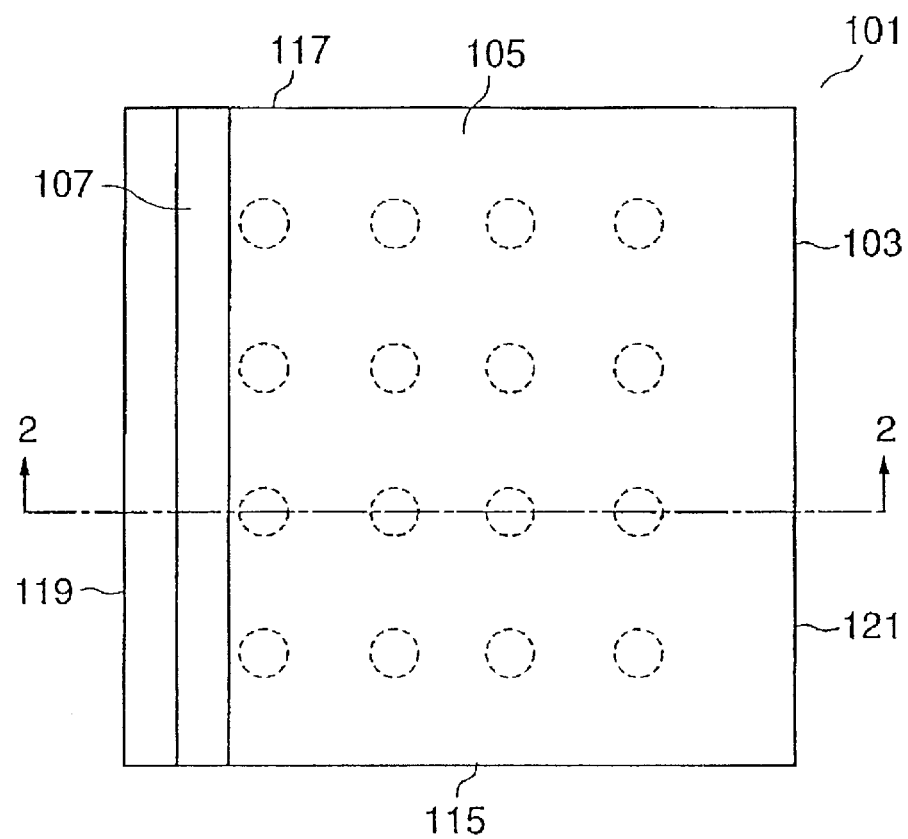
FIG. 1 is a plan perspective view showing the back of a semiconductor device 101 according to a first embodiment of the present invention.

A semiconductor device according to preferred embodiments of the present invention will be explained hereinafter with reference to the figures. In order to simplify the explanation, like elements are given like or corresponding reference numerals through this specification and figures. Dual explanations of the same elements are avoided.

First Preferred Embodiment

Figure 2:
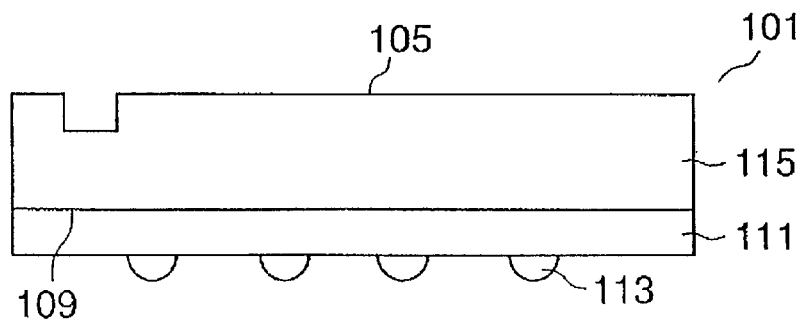
FIG. 2 is a schematic cross-sectional view taken along line 2—2 of FIG. 1.

FIG. 1 is a plan perspective view showing the back of a semiconductor device 101 according to a first embodiment of the present invention, and FIG. 2 is a schematic cross-sectional view taken along line 2—2 of FIG. 1, respectively.

The semiconductor device 101 corresponds to the WCSP as mentioned previously. The semiconductor device 101 has a semiconductor substrate 103 (also called a "semiconductor chip"), a sealing resin 111, and a plurality of protruded electrodes 113.

As shown in FIGS. 1 and 2, the semiconductor device 101 has outer dimensions approximately identical to those of the semiconductor chip. In the present embodiment, the semiconductor device 101 is shaped in the form of a substantially quadrangle whose one side is 8 mm, for example.

The semiconductor substrate 103 has a surface 109 (first main surface) with circuit elements formed thereon, a reverse side or back 105 (second main surface) substantially opposite to the surface 109, and a plurality of side faces which connect between the surface 109 and the back 105. Further, the semiconductor substrate 103 has a steplike section 107 (also called a "concave portion, trench portion or slit") formed in the back 105. The steplike section 107 indicates a characteristic portion of the present invention. The steplike section 107 is formed in the back 105 so as to extend from a first side face 115 of the semiconductor substrate 103 to a second side face 117 opposite to the first side face 115. Further, the steplike section 107 is formed in the back 105 in the vicinity of a third side face 119 adjacent to the first and second side faces. Here, the terms of "the neighborhood of the third side face 119 with the steplike section 107 formed thereat" means a location placed on the third side face 119 side as viewed from the center of the semiconductor substrate 103.

The sealing resin 111 is formed on the surface 109 of the semiconductor substrate 103 and has the function of protecting unillustrated circuit elements formed on the surface 109 from external environments.

The plurality of protruded electrodes 113 are respectively formed on unillustrated posts formed inside the sealing resin 111 and electrically connected to their corresponding circuit elements formed on the semiconductor substrate 103 by means of the posts. These protruded electrodes 113 serve as external terminals of the semiconductor device 101. Incidentally, the posts will be described in detail later.

Figure 3:
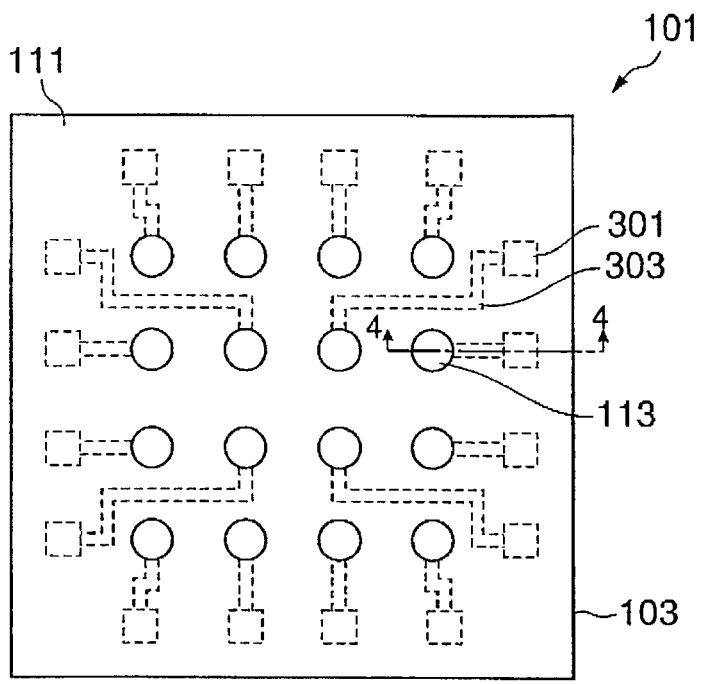
FIG. 3 is a plan perspective view illustrating the surface of the semiconductor device 101 according to the first embodiment of the present invention.
Figure 4:
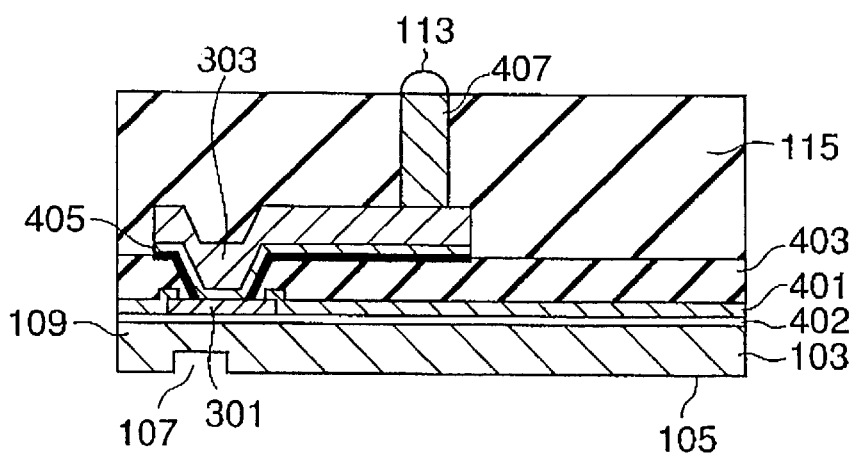
FIG. 4 is a detailed cross-sectional view taken along line 4—4 of FIG. 3.

FIG. 3 is a plan perspective view showing the surface of the semiconductor device 101 according to the first embodiment of the present invention, and FIG. 4 is a detailed cross-sectional view taken along line 4—4 of FIG. 3, respectively.

Electrode pads 301, metal wiring layers 303 and protruded electrodes 113 are illustrated in FIG. 3. Since the electrode pads 301 and the metal wiring layers 303 are located below the sealing resin 111, they are indicated by dotted lines respectively.

As shown in FIG. 3, the sixteen electrode pads 301 are provided in a peripheral area of the surface 109 of the semiconductor substrate 103 at intervals of 100 $\mu$m, for example.

The sixteen protruded electrodes 113 are disposed in matrix form on a central area of the surface 109 of the semiconductor substrate 103. The respective protruded electrodes 113 are electrically connected to their corresponding metal wiring layers 303 via unillustrated posts.

The metal wiring layers 303 performs the function of substantially shifting the positions of external terminals from a peripheral portion of the semiconductor substrate 103 to a central area of the semiconductor substrate 103. In general, such shift is called "relocation". Therefore, the metal wiring layers 303, which perform such shift, are called "relocating wirings or rewirings". They may also be known as "redistribution" conductors. Placing the protruded electrodes 113 serving as the external terminals in the central area of the semiconductor substrate 103 in this way allows a size reduction in the printed circuit board connected to the semiconductor device 101.

A configuration of the semiconductor device 101 will next be described in more detail by using FIG. 4.

Unillustrated plural circuit elements are formed on a surface 109 (first main surface) of a semiconductor substrate 103 made up of silicon. A steplike section 107 is provided at the back 105 (second main surface) of the semiconductor substrate 103. An insulating layer 402 having contact holes (not shown) is formed over the respective circuit elements. An unillustrated conductive layer is formed inside each contact hole.

An electrode pad 301 is formed on the insulating layer 402. The electrode pad 301 is connected to its corresponding circuit element through the conductive layer formed inside the contact hole. The electrode pad 301 is made up of aluminum containing silicon, for example.

A passivation film 401 is formed over the insulating layer 402 and a peripheral edge portion of the electrode pad 301. The passivation film 401 comprises silicon nitride, for example.

An interlayer insulator or dielectric 403 is formed over the passivation film 401. The interlayer dielectric 403 has the function of relaxing stress applied to the semiconductor substrate 103. The interlayer dielectric 403 is made up of polyimide, for example. Incidentally, the surface of the interlayer dielectric 403 located just below a metal thin-film layer 405 to be described later changes in quality. A thick line indicates an area in which the surface thereof has changed in quality. The existence of the interlayer dielectric 403 whose surface has changed in quality, yields an improvement in adhesion between the interlayer dielectric 403 and the metal thin-film layer 405.

The metal thin-film layer 405 is formed over the interlayer dielectric 403 and the electrode pad 301. The metal thin-film layer 405 may be either a single layer or a complex layer but may preferably be formed of a complex layer comprising an upper layer and a lower layer. The lower film may be a material high in adhesion to the electrode pad 301 and capable of preventing a substance constituting the upper film from diffusing into the semiconductor substrate 103 side. The lower film is made of titanium, for example. The upper film may be a material high in adhesion to the metal wiring layer 303 formed thereabove. The upper film comprises copper, for example.

The metal wiring layer 303 is formed on the metal thin-film layer 405. The metal wiring layer 303 is made of copper, for example.

A post 407 is formed on the surface of the metal wiring layer 303. In the illustrated example, the post 407 is shaped in the form of a substantially cylinder. The bottom face of the post 407 makes contact with the surface of the metal wiring layer 303, and the top thereof is in contact with the protruded electrode 113. The post 407 is made of the same material as the metal wiring layer 303, and the height (corresponding to the distance from the surface of the metal wiring layer 303 up to the surface of an sealing resin 115) thereof is about 100 μm.

The sealing film 115 is formed over the entire surface 109 of the semiconductor substrate 103 so as to cover the whole surface 109 of the semiconductor substrate 103 except for the top of the post 407. Namely, the sealing resin 115 covers the side faces of the interlayer dielectric 403, metal thin-film layer 405, metal wiring layer 303 and post 407. The surface of the sealing resin 115 and the top of the post 407 are flush with each other. The sealing resin 115 is made up of an opaque epoxy resin, for example.

The protruded electrode 113 is formed on the top of the post 407. The protruded electrode 113 is an electrode connected to its corresponding wiring of an unillustrated printed circuit board as will be described later. Thus, at least one circuit element formed on the semiconductor substrate 103 is electrically connected to an external device through the electrode pad 301, metal thin-film layer 405, metal wiring layer 303, post 407 and protruded electrode 113. Thus, the protruded electrode 113 functions as an external terminal of the semiconductor device 101. The protruded electrode 113 is made of solder, for example. Further, the protruded electrode 113 is shaped in the form of a semicircular sphere whose diameter is 400 μm.

A method of mounting or packaging a semiconductor device 101 on a mounting board or printed circuit board 501 will next be described below with reference to FIGS. 5 and 6.

Figure 5:
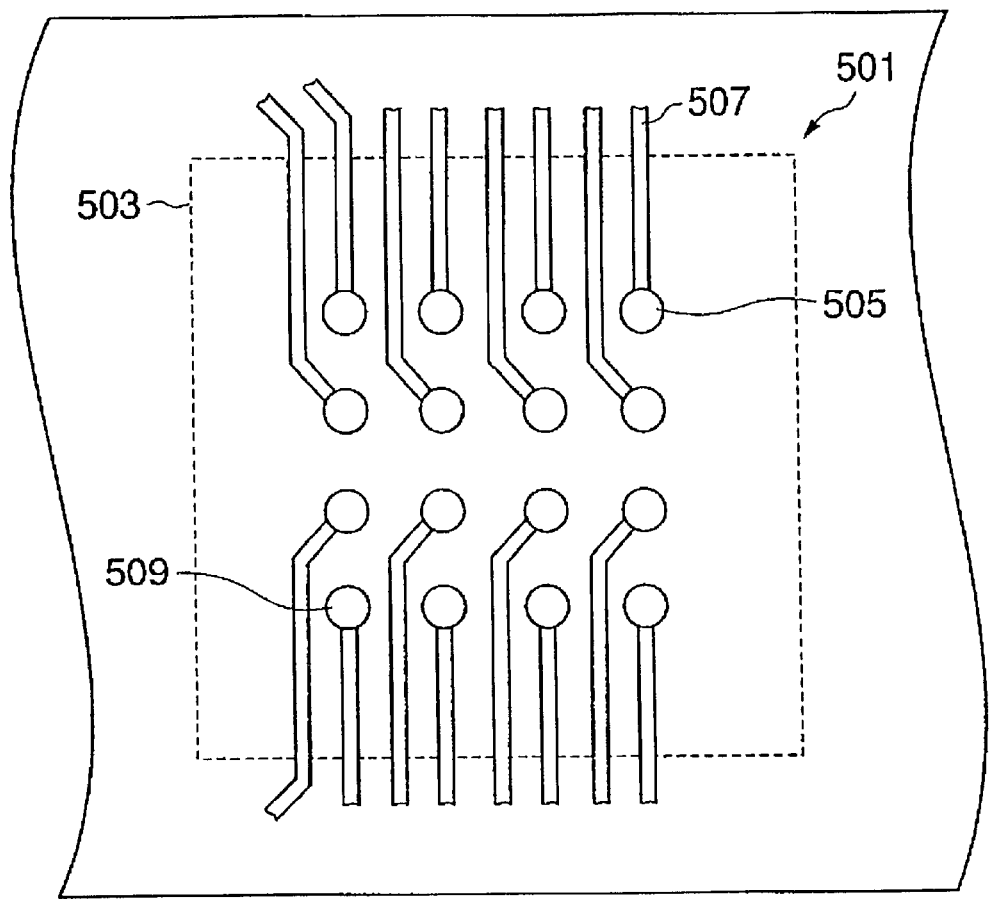
FIG. 5 is a plan view showing a printed circuit board 501.

FIG. 5 is a plan view showing the printed circuit board 501.

A plurality of terminals 505 corresponding to a plurality of protruded electrodes 113 of the semiconductor device 101 are formed on the surface of the printed circuit board 501 in matrix form. The terminal 509 corresponding to each specific terminal, of the plurality of terminals 505 is placed in the lower left as viewed in the drawing. The terminal 509 is a terminal corresponding to an address signal A1, for example, and is a terminal called a "first terminal".

Corresponding wirings 507 are connected to the respective terminals 505. These wirings 507 are connected to an unillustrated other device mounted on the printed circuit board 501, for example.

A mounting area 503 is indicated by a dotted line. The mounting area 503 is an area on which the semiconductor device 101 is to be mounted. The dotted line indicates an outer shape of the semiconductor device 101.

Figure 6:
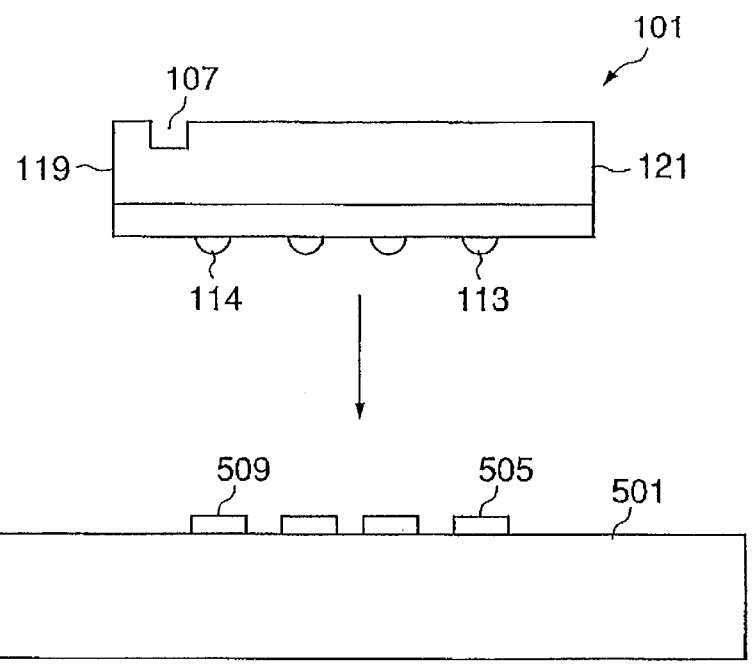
FIG. 6(a) and FIG. 6(b) are process diagrams illustrating a process for mounting the semiconductor device 101 over the printed circuit board 501.
Figure 6:
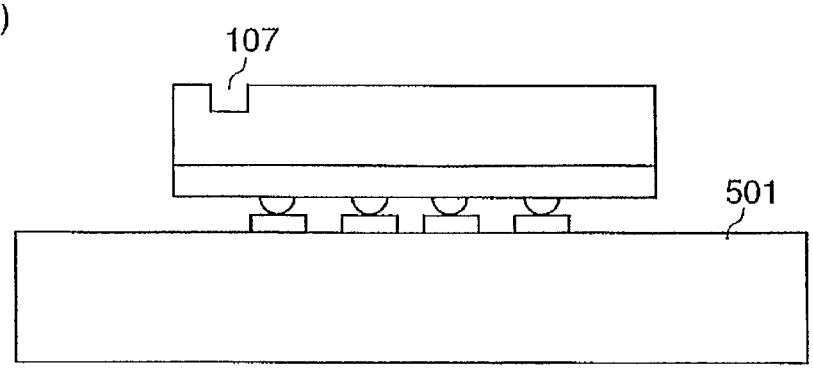

FIG. 6 is a process diagram showing a process for mounting a semiconductor device 101 over a printed circuit board 501. This process will be described with reference to FIG. 6.

Specific protruded electrodes 114 of a plurality of protruded electrodes 113 of the semiconductor device 101 are external terminals each corresponding to an address signal A1, for example, which each terminal will be called a "first pin". The semiconductor device 101 like a WCSP is fractionized from a semiconductor wafer and thereafter temporarily accommodated in a tray. However, it is necessary to accommodate the fractionized semiconductor devices 101 in the tray with the directions thereof placed in alignment in consideration of a subsequent mounting process. Namely, it is necessary to accommodate each semiconductor device 101 within the tray so that the positions of the first pins of the semiconductor device 101 are all placed in the lower left, for example, within the tray.

Each of the semiconductor devices 101 is accommodated in the tray by use of an auto handler provided with an image recognizer. A steplike section 107 is formed in a back 105 near a side face 119 closest from the first pin. Thus, the auto handler recognizes the position of the steplike section 107, whereby it accommodates the semiconductor device 101 within the tray so that the positions of the first pins of the semiconductor device 101 are all placed in the lower left.

In the prior art, the laser has been used to form the marks each called "one pin mark" indicative of the position of each first pin. Thus, when light is applied to the back of the semiconductor substrate, the difference between the intensity of light reflected by the portion subjected to marking and returned to the image recognizer and the intensity of the light reflected by the portion free of marking and returned to the image recognizer is small. Namely, the light incident from the image recognizer to the back of the image recognizer is returned to the image recognizer as the reflected light without being substantially scattered. Thus, it was hard to recognize each mark even if the image recognizer has been used.

According to the present embodiment, however, even if the back of the semiconductor substrate 103 is held in a mirror state where light is applied to the back of the semiconductor substrate, the intensity of the light reflected by the steplike section 107 and returned to the image recognizer becomes smaller than that of the light reflected by the back held in the mirror state and returned to the image recognizer. This is because the incident light is reflected diffusely by a step of the steplike section 107. Further, the steplike section 107 is formed by a dicing blade as will be described later. Thus, the state of the surface of the steplike section 107 is rougher than other area (back held in the mirror state) of the back of the semiconductor substrate 103. Therefore, the intensity of the light reflected by the surface kept in the rough state and returned to the image recognizer becomes smaller than that of the light reflected by the back held in the mirror state and returned to the image recognizer. This is also because the incident light is reflected diffusely by the surface kept in the rough state after all.

Thus, the image recognizer attached to the auto handler can detect the difference between the intensities of the reflected lights referred to above to thereby easily detect the orientation or direction of the semiconductor device 101. As a result, each semiconductor device 101 can be accommodated in the tray accurately and at high speed.

The semiconductor device 101 held in the tray as described above is taken out from the tray by the automatic mounting or packaging device provided with the image recognizer. Since the present automatic mounting device is also provided with the image recognizer as a matter of course, the direction of the semiconductor device 101 is recognized by the automatic mounting device. As shown in FIG. 6(a), the taken-out semiconductor device 101 is placed above the printed circuit board 501 by the automatic mounting device. At this time, the semiconductor device 101 is located face to face with the printed circuit board 501 so that the first pins 114 and the first terminals 509 correspond to each other.

Next, as shown in FIG. 6(b), the protruded electrodes 113 of the semiconductor device 101 are connected to their corresponding plural terminals 505 of the printed circuit board 501. The mounting process is completed in this way.

Subsequently, a visual inspecting process for inspecting whether the semiconductor device 101 is placed on the printed circuit board 501 in a proper orientation, is executed. The visual inspecting process is carried out by a visual inspecting device provided with an image recognizer. According to the present embodiment as described above, even if the back of the semiconductor substrate 103 is held in the mirror state, the orientation of the semiconductor device 101 can easily be detected owing to the steplike section 107 attached to the semiconductor substrate 103. Thus, the mispackaging of the semiconductor device 101 can be determined accurately and at high speed even upon such a visual inspecting process.

According to the present invention as described above in detail, the direction of each semiconductor device 101 can accurately be recognized in all the processes such as the process of accommodating each semiconductor device 101 in the tray, the process of taking out it therefrom, and the process of mounting it to the printed circuit board. Incidentally, it can easily be understood by those skilled in the art that even if the recognizing work in the above processes is visually carried out by a human being, a similar effect can be obtained.

Figure 12:
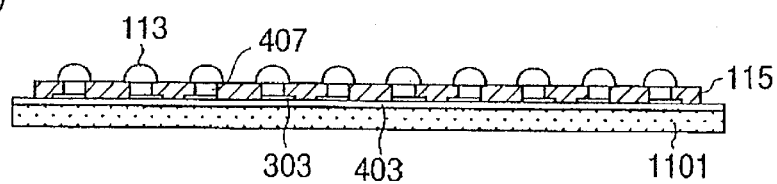
FIG. 12(A) and FIG. 12(E) are process diagrams illustrating a second process used for the semiconductor device 101 according to the first embodiment of the present invention.
Figure 12:
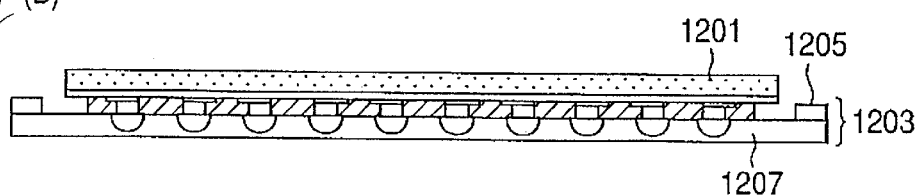
Figure 12:
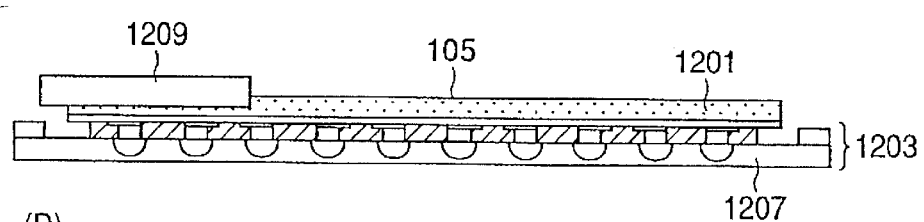
Figure 12:
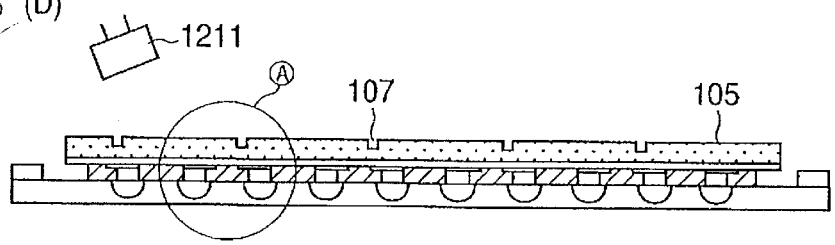
Figure 12:
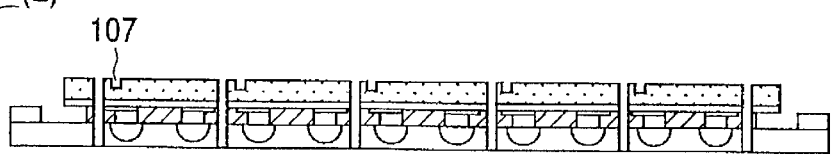
Figure 13:
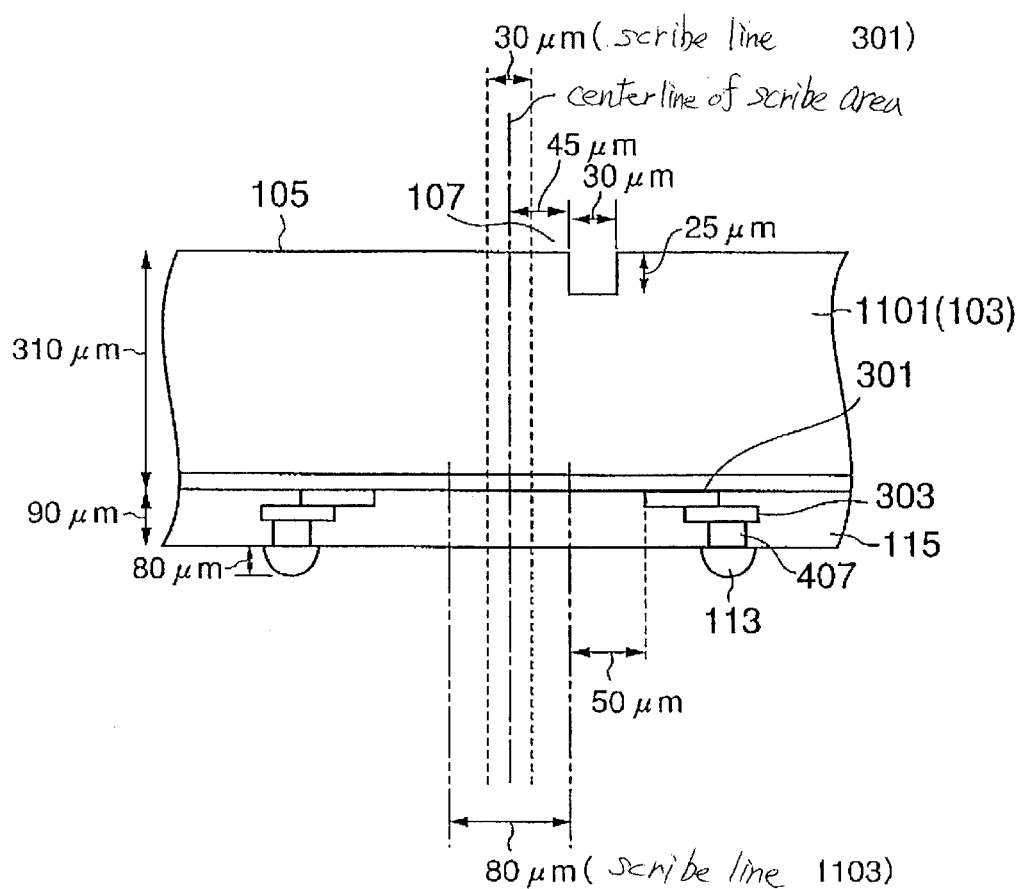
FIG. 13 is a diagram depicting a schematic cross-section of a portion indicated by a round mark "A" in a process step of FIG. 12(D).
Figure 14:
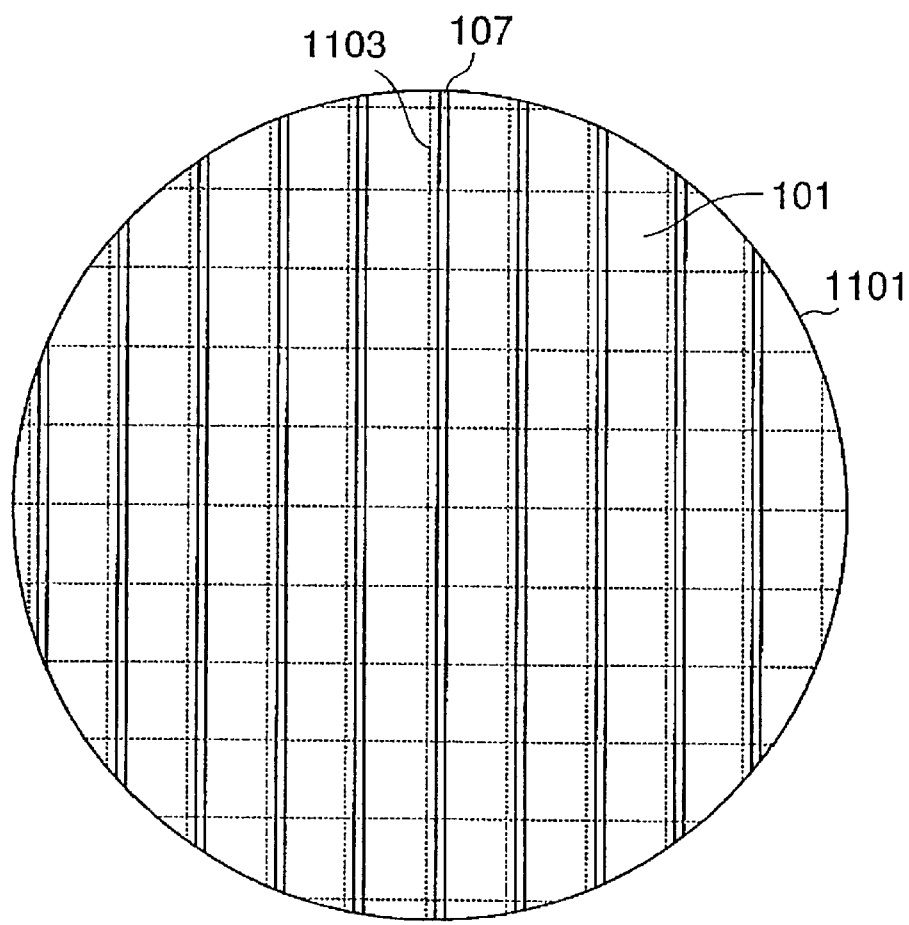
FIG. 14 is a diagram showing the reverse side of a semiconductor wafer 1101 in the process step of FIG. 12(D).

A method of manufacturing the semiconductor device 101 according to the first embodiment of the present invention will next be described below. In order to make its description easy, a process (corresponding to a process prior to the dicing of the semiconductor wafer) up to the formation of the protruded electrodes 113 is called a "first process", and a process subsequent to the first process is called a "second process". They will be described below respectively. The first process is shown in FIGS. 7 through 10, and the second process is shown in FIGS. 12 through 14.

To begin with, the first process according to the first embodiment will be explained below.

Incidentally, only a portion corresponding to line 4—4 of FIG. 3 will be explained in the first process for the purpose of making its description easy.

Unillustrated plural circuit elements are first formed on a surface 109 (first main surface) of a semiconductor substrate 103 held in a semiconductor wafer state. Next, an insulating layer 402 having contact holes (not shown) is formed over the respective circuit elements. An unillustrated conductive layer is formed inside each contact hole. Subsequently, an aluminum film containing silicon is deposited on the insulating layer 402 by a sputtering method. Afterwards, the aluminum film is etched into a predetermined shape, which in turn is left on the insulating layer 402 as an electrode pad 301 as shown in the drawing. The electrode pad 301 is connected to its corresponding unillustrated conductive layer formed inside the insulating layer 402 (see FIG. 7(A)).

Next, a passivation film 401 made up of a silicon nitride film is formed on the insulating layer 402 and the electrode pad 301 by a CVD method. Thereafter, the passivation film 401 placed on a central area of the electrode pad 301 is removed by etching (see FIG. 7(B)).

Figure 7A:
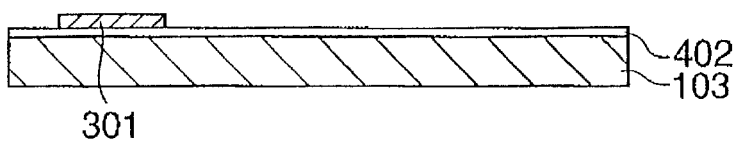
FIG. 7(A) and FIG. 7(G) are process diagrams depicting a method of manufacturing the semiconductor device 101 according to the first embodiment of the present invention.
Figure 7B:
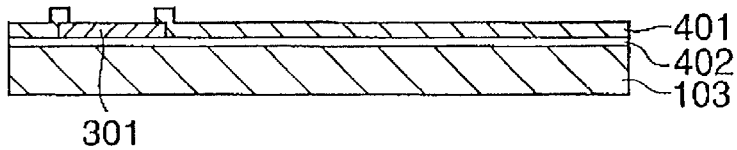
Figure 7C:
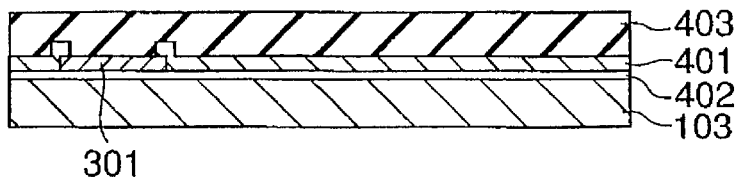

Next, an interlayer dielectric or insulator 403 formed of polyimide is formed on the passivation film 401 and the electrode pad 301 (see FIG. 7(C)).

Figure 7D:
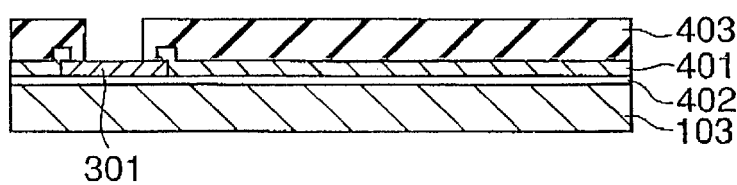
Figure 7E:
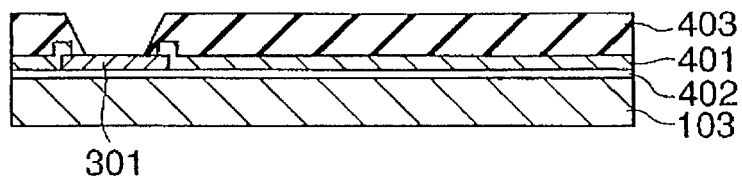
Figure 7F:
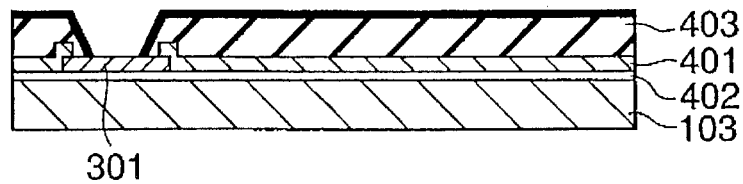

Next, the interlayer insulator 403 placed in the central area of the electrode pad 301 is removed by etching (see FIG. 7(D)).

Heat treatment is next made to thermoset the interlayer insulator 403 formed of polyimide. Owing to such thermosetting, the interlayer insulator 403 located on the electrode pad 301 is shaped in tapered form as shown in the drawing. When polyimide exists on the surface of the electrode pad 301, it is removed by plasma etching in an oxygen atmosphere (see FIG. 7(E)).

Next, the interlayer insulator 403 is subjected to plasma etching in an atmosphere of an inert gas such as an argon gas or the like, so that the surface of the interlayer insulator 403 changes in quality. A surface layer thereof having changed in quality, is indicated by a thick line. The existence of the surface layer yields an improvement in adhesion to a metal thin-film layer 405 formed in the following step (see FIG. 7F).

Figure 7G:
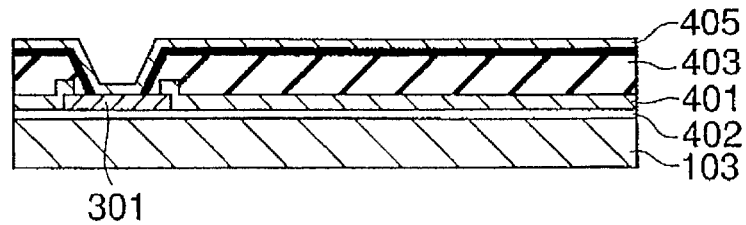

Next, the metal thin-film layer 405 is formed on the interlayer insulator 403 and the electrode pad 301 by the sputtering method (see FIG. 7(G)).

A resist 801 is next formed on the metal thin-film layer 405. The thickness of the resist is about 10 $\mu$m, for example. Subsequently, the resist 801 located in an illustrated predetermined area is removed by etching (see FIG. 8(A)).

Next, a metal wiring layer 303 is selectively formed on the metal thin-film layer 405 exposed by electrolytic plating. Incidentally, the thickness of the metal wiring layer 303 is thinner than that of the resist 801 and is 5 $\mu$m, for example (see FIG. 8(B)).

Figure 8A:
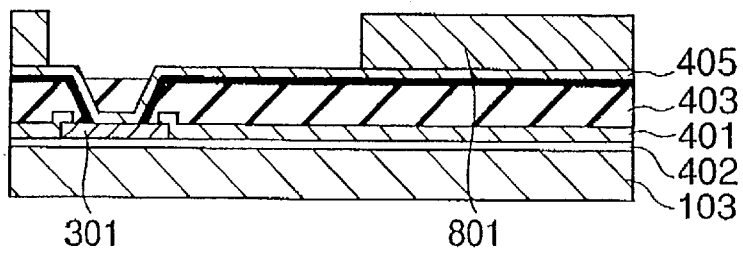
FIG. 8(A) and FIG. 8(E) are process diagrams showing the method of manufacturing the semiconductor device 101 according to the first embodiment of the present invention.
Figure 8B:
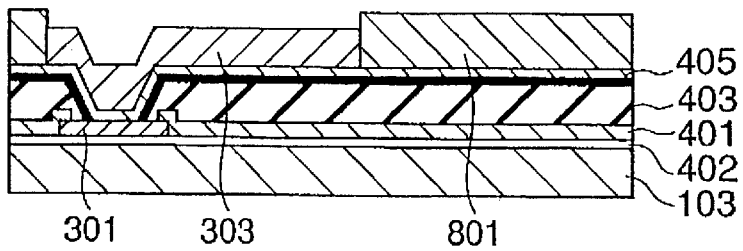
Figure 8C:
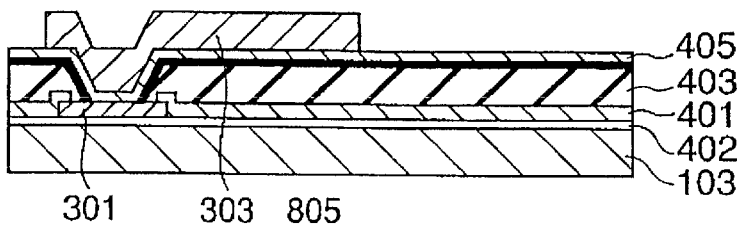
Figure 8D:
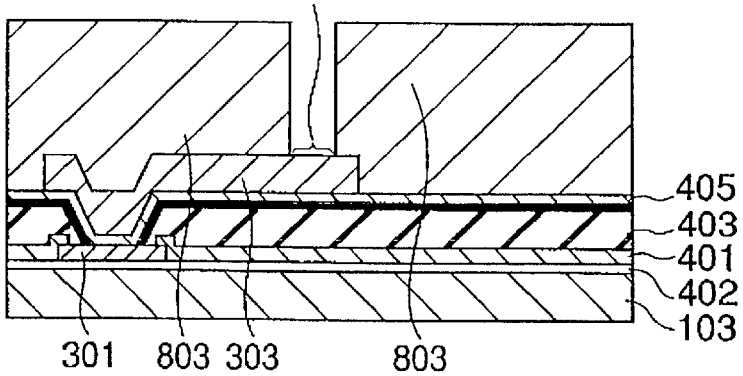
Figure 8E:
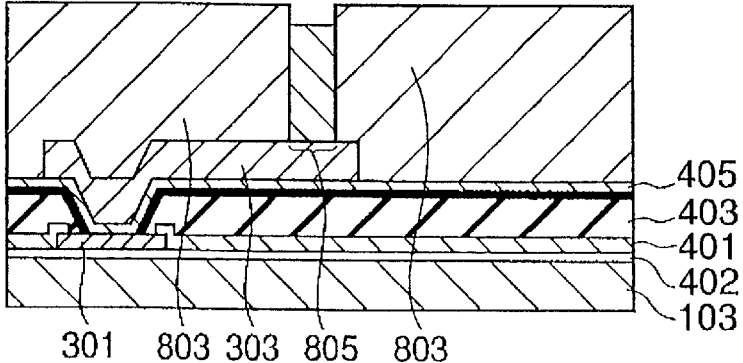

Next, the resist 801 is removed by using a remover such as acetone or the like (see FIG. 8(C)).

Next, a resist 803 having a thickness of about 120 µm is formed on the metal thin-film layer 405 and the metal wiring layer 303. Subsequently, the resist 803 placed on a post forming area 805 is removed.

A post 407 is next formed on the post forming area 805 by the electrolytic plating. Incidentally, the thickness of the post 407 is thinner than that of the resist 803 and is about 100 µm. Further, the post 407 is formed of the same material as the metal wiring layer 303. Thus, the plating solution used in FIG. 8(B) can be used (see FIG. 8(D)).

Figure 9A:
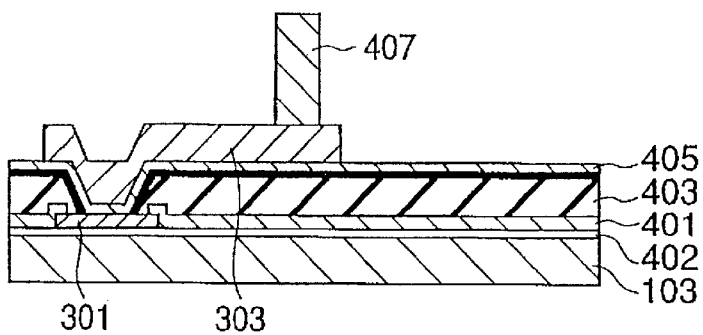
FIG. 9(A) and FIG. 9(D) are process diagrams illustrating the method of manufacturing the semiconductor device 101 according to the first embodiment of the present invention.

Next, the resist 805 is removed by a remover (see FIG. 9(A)).

Figure 9B:
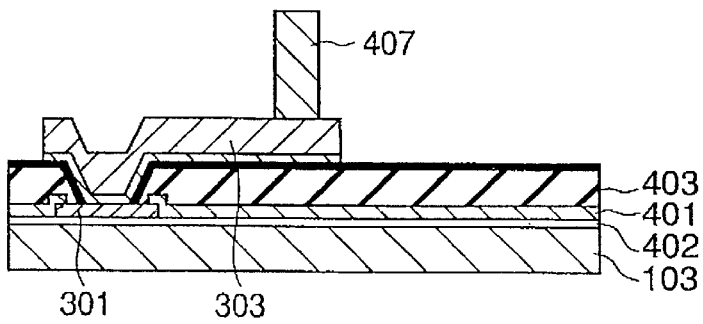
Figure 9C:
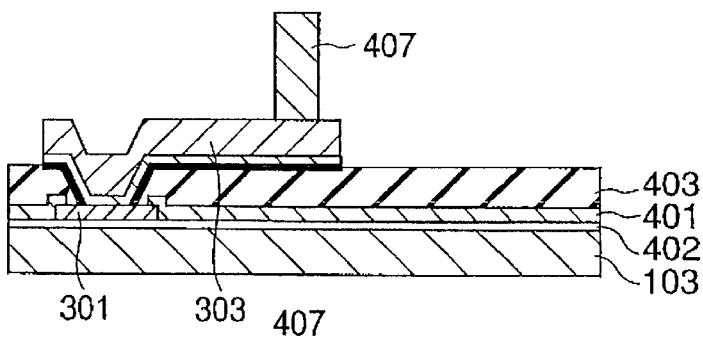
Figure 9D:
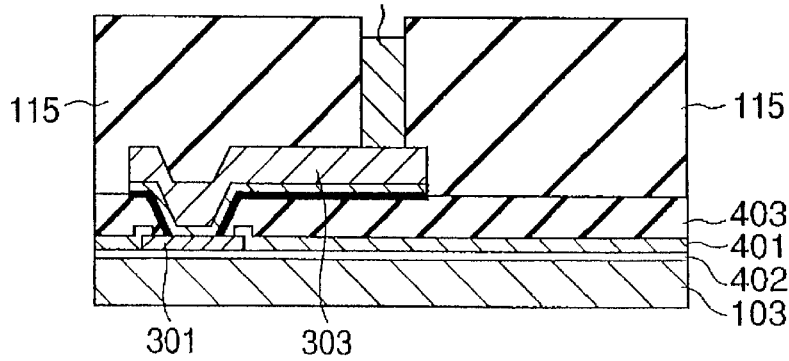
Figure 10:
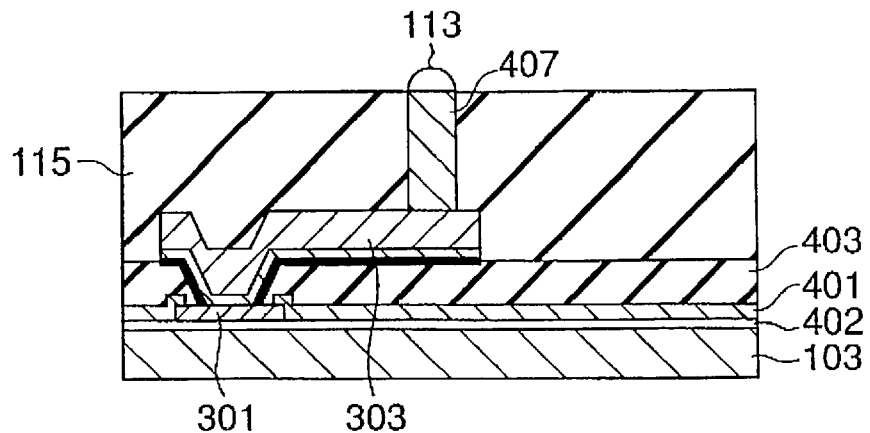
FIG. 10 is a process diagram depicting a first process used for the semiconductor device 101 according to the first embodiment of the present invention.

Next, the exposed metal thin-film layer 405 is removed by being exposed to plasma etching in an atmosphere of an oxygen gas (FIG. 9(B)).

Next, the surface layer of the exposed interlayer insulator 403 is removed by wet etching. Thus, a current, which flows in the metal wiring layer 303, can be prevented from leaking into another metal wiring layer 303 through the surface layer (see FIG. 9(C)).

Next, the whole semiconductor wafer is inserted into an unillustrated sealing mold. With the injection of an sealing resin inside the sealing mold, an sealing resin 115 is subsequently formed on the surface 109 side of the semiconductor substrate 103. As shown in the drawing, the sealing resin 115 covers the side faces of the interlayer insulator 403, the metal thin-film layer 405, the metal wiring layer 303 and the post 407 (see FIG. 9(D)).

Next, the surface of the sealing resin 115 is polished to expose an upper surface of the protruded electrode 113. The surface of the sealing resin 115 and the upper surface of the protruded electrode 113 are located within the same plane.

Next, the protruded electrode 113 is formed on its corresponding upper surface of the post 407 by a screen printing method. The protruded electrode 113 is made up of solder and is a hemisphere having a diameter of about 400 µm (see FIG. 10).

Figure 11:
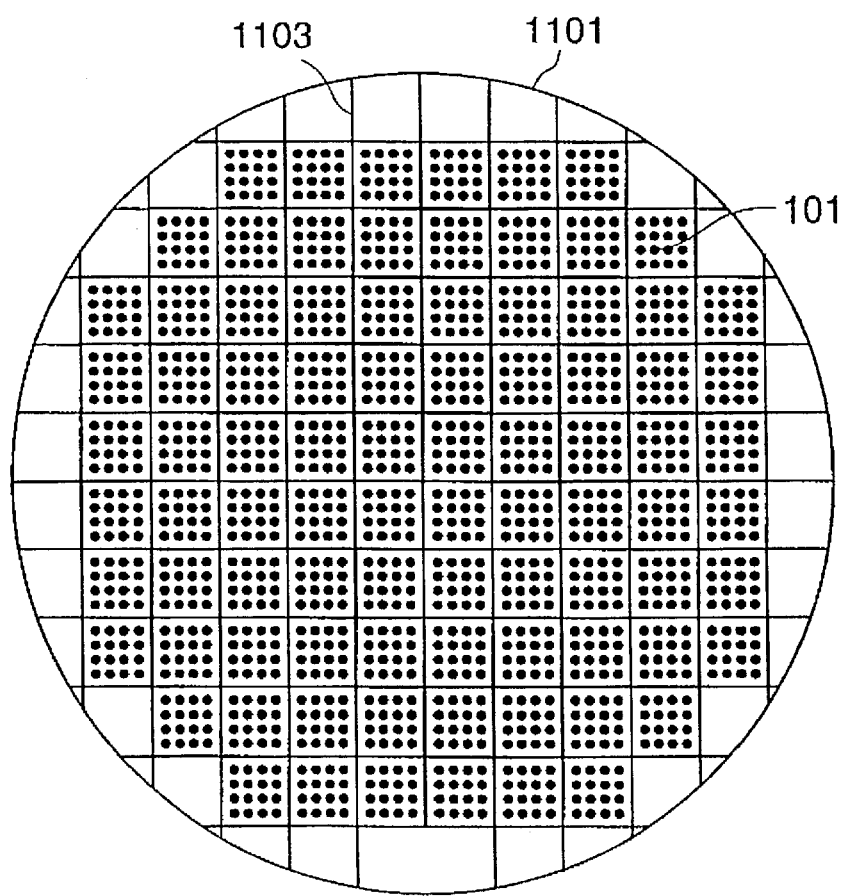
FIG. 11 is a plan view showing the surface side of a semiconductor wafer 1101.

The surface side of a semiconductor wafer 1101 subjected to the above-described process is shown in FIG. 11. FIG. 11 shows that a plurality of semiconductor devices 101 fractionized in the second process to be described later are disposed in a semiconductor wafer state. These semiconductor devices 101 are spaced away from one another by a plurality of scribe areas 1103. Incidentally, since steplike sections 107 are not yet provided at the backs of the respective semiconductor devices 101, the illustration of the back side of the semiconductor wafer will be omitted.

The second process following the first process referred to above will next be explained below using FIG. 12.

FIG. 12 is a process diagram showing the second process for the semiconductor device 101 according to the present embodiment. Incidentally, the illustration of part of a structure thereof is omitted in order to facilitate its description.

Firstly, the state of the semiconductor device 101 subjected to the process of from FIG. 7 to FIG. 10 is shown in FIG. 12(A).

A semiconductor wafer 1101, an interlayer dielectric or insulator 403, a metal wiring layer 303, posts 407 and protruded electrodes 113 are shown in FIG. 12(A).

A wafer holder 1203 having a wafer ring 1205 and a dicing sheet 1207 is next prepared. The wafer ring 1205 has a ring shape. The dicing sheet 1207 makes use of a UV tape having such a characteristic that it is reduced in adhesive power by being irradiated with ultraviolet light or rays, for example.

The semiconductor wafer 1101 is attached over the dicing sheet 1207 so that the protruded electrodes 113 make contact with the dicing sheet 1207 (see FIG. 12(B)).

Next, the wafer holder 1203 is placed on an unillustrated grinder having two diamond grinding stones 1209. The first diamond grinding stone 1209 has roughness of #325, and the second diamond grinding stone 1209 has roughness of #2000. The back of the semiconductor wafer 1101 placed on the grinder is ground as follows: To begin with, the back thereof is roughly polished by the first diamond grinding stone, and subsequently finely ground by the second diamond grinding stone. Owing to these grinding processes, a semiconductor wafer 1101 having a thickness of about 310 µm is finally obtained.

Further, owing to the grinding done by the second diamond grinding stone, the back of the semiconductor wafer is brought into the aforementioned mirror state. If such fine back grinding is not done, then the mirror state might not be produced. However, the detection of each scribe area by an infrared camera in a process step of FIG. 12(D) needs the fine grinding by the second diamond grinding stone. This is because if the state of the back of the semiconductor substrate 103 is rough, then infrared light is not easily transmitted therethrough (see FIG. 12(C)).

Next, the semiconductor wafer 1101 is placed on a dual dicing device with an unillustrated infrared camera 1211 in a state of being placed on the wafer ring 1205. The dual dicing device has two blades provided side by side. In the present embodiment, a first blade and a second blade which are rectangular in sectional shape and are both 30 µm in thickness, are used.

FIG. 13 shows a schematic cross-section of a portion to which a round mark "A" in FIG. 12(D) is affixed. The width of each scribe area 1103 is defined as about 80 µm. The distance between the edge of the scribe area 1103 and the edge of each electrode pad 301 is defined as about 50 µm. The width of each scribe line 1301 to be cut later is about 30 µm substantially identical to that of the first blade. Each of steplike sections 107 formed in the process step of FIG. 12(D) is formed at a position distant about 45 µm from the center line of the scribe area. The width of each steplike section 107 is about 30 µm identical to the width of the second blade, and the depth thereof is about 25 µm.

As shown in FIG. 12(D), pattern shapes of a plurality of electrode pads 301 or metal wiring layers 303 formed on the surface 109 side of the semiconductor wafer are first recognized from the back of the semiconductor wafer 1101 by the infrared camera 1211. Consequently the scribe areas 1103, which exist on the surface 109 of the semiconductor wafer 1101, are recognized by the dicing device.

Next, the second blade is placed at a position spaced about 45 µm away from the center line of each scribe area 1103. Thereafter, the back 105 of the semiconductor wafer 1101 is ground (half-cut) about 25 µm by the second blade so that each steplike section 107 is formed (see FIG. 13). The surface of the steplike section 107 is coarser than the other back 105 of the semiconductor wafer 1101 (semiconductor substrate 103) held in the mirror state due to the grinding done by the second blade. The grinding by the second blade is carried out in association with the respective semiconductor devices 101 of the semiconductor wafer 1101 (see FIG. 12(D)). FIG. 14 is a diagram showing the back side of the semiconductor wafer 1101 in the process step of FIG. 12(D). It can be understood that the steplike sections 107 formed by the second blade are formed in the vicinity of one sides of the respective semiconductor devices 101.

Next, the first blade is placed on the center line of each scribe area 1103, i.e., the scribe line 1301. Thereafter, the back 105 of the semiconductor wafer 1101 is ground (fully cut) about 400 µm along each scribe line 1301 by the first blade. The grinding by the first blade is executed in association with the respective semiconductor devices 101 of the semiconductor wafer 1101. As a result, the respective semiconductor devices 101 are brought into fractionalization (see FIG. 12(E)).

Next, the semiconductor wafer 1101 is shifted to an expand ring together with the dicing sheet 1207. Thereafter, the dicing sheet 1207 is subjected to ultraviolet rays, so that its adhesive power is lowered. The dicing sheet 1207 is extended in the outer peripheral direction of the semiconductor wafer 1101 and the respective semiconductor devices 101 are taken out by a collet.

The semiconductor device 101 shown in FIGS. 1 and 2 is finally obtained through the above-described second process.

While the effect of the semiconductor device according to the present invention has already been described above, the present invention has a peculiar effect even with respect to a manufacturing method thereof. Namely, since the steplike section 107 indicative of the direction of each semiconductor device can be formed by the blades used in the dicing process, a specific process for providing the steplike section 107 is substantially unnecessary. It is thus possible to obtain the semiconductor device without substantially providing the specific process.

Figure 15:
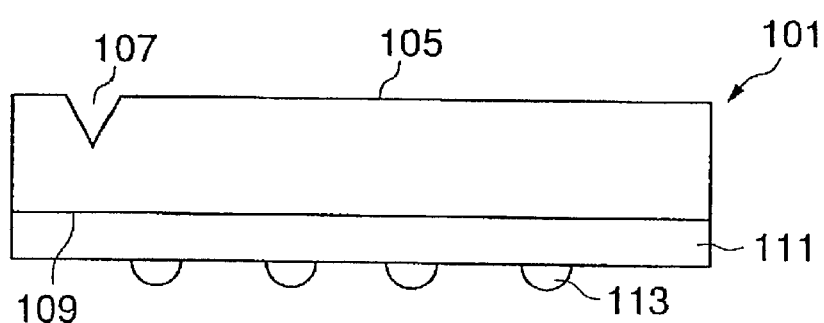
FIG. 15 is a diagram illustrating a modification of the semiconductor device according to the first embodiment of the present invention.
Figure 16:
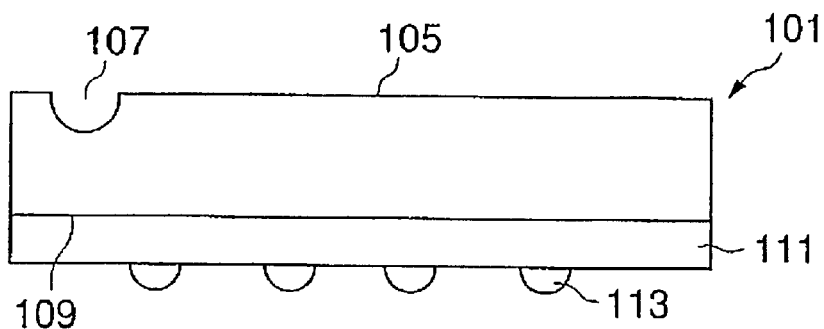
FIG. 16 is a diagram depicting another modification of the semiconductor device according to the first embodiment of the present invention.

Incidentally, the steplike section 107 according to the present invention may take such shapes as shown in FIGS. 15 and 16 as well as such a shape as shown in FIG. 2. In this case, a second dicing blade having a V-shaped or U-shaped cross-section is used. In short, the steplike section 107 may have a depth equivalent to such an extent that it can be distinguishable from the back 105 of the flat semiconductor substrate held in the mirror state. Alternatively, the steplike section 107 may take roughness equivalent to such an extent that it can be distinguishable from the back 105 of the flat semiconductor substrate held in the mirror state.

Second Preferred Embodiment

A second embodiment showing a semiconductor device of the present invention will next be described below with reference to the accompanying drawings.

Figure 17:
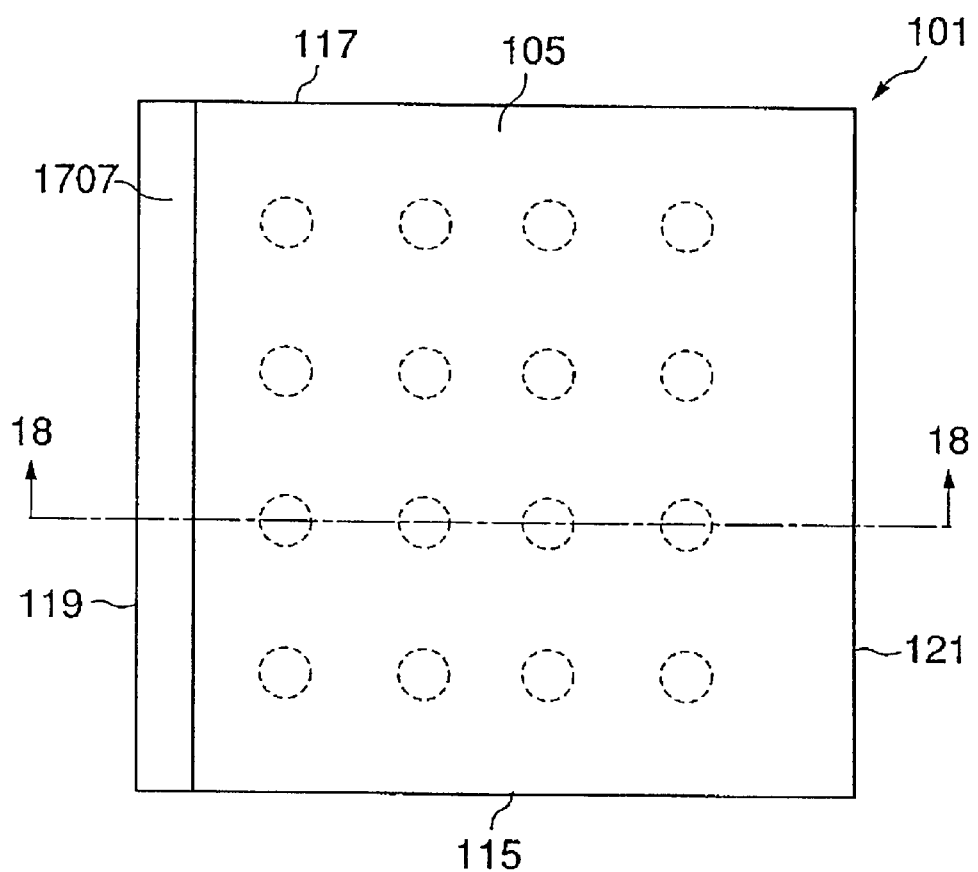
FIG. 17 is a plan perspective view showing the back of a semiconductor device according to a second embodiment of the present invention.
Figure 18:
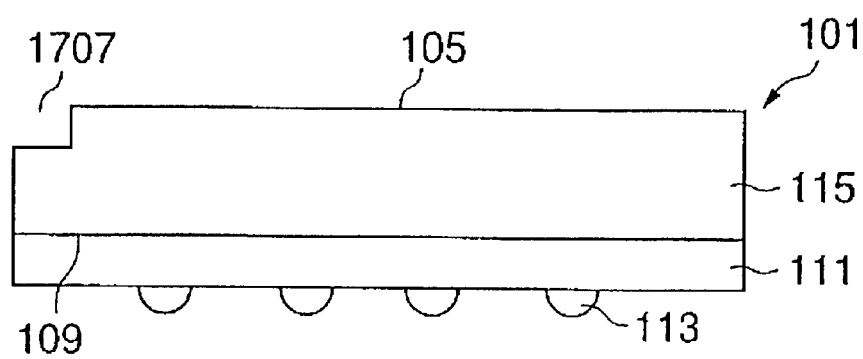
FIG. 18 is a schematic cross-sectional view taken along line 18—18 of FIG. 17.

FIG. 17 is a plan perspective view showing the second embodiment of the semiconductor device 101 of the present invention, and FIG. 18 is a schematic cross-sectional view taken along line 18—18 of FIG. 17, respectively.

The second embodiment is different from the first embodiment in terms of both the shape of a steplike section 1707 and its manufacturing method. Since the second embodiment is substantially identical to the first embodiment in other configurations, the detailed description thereof will be omitted.

As shown in FIGS. 17 and 18, a semiconductor substrate 103 has a steplike section 1707 (also called a "concave portion or trench portion") formed in a reverse side or back 105. The steplike section 1707 is a characteristic portion of the present invention. The steplike section 1707 is formed so as to extend from a first side face 115 of the semiconductor substrate 103 to a second side face 117 opposite to the first side face 115. Further, the steplike section 1707 is formed in the back 105 along a third side face 119 adjacent to the first and second side faces. Here, the term of "along the third side face 119" means that the steplike section 1707 is formed in the back 105 with the third side face 119 as a starting point, or the steplike section 1707 is formed in the back 105 by grinding some of the third side face 119.

Figure 19A:
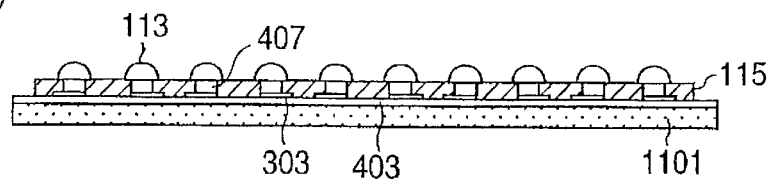
FIG. 19(A) and FIG. 19(E) are process diagrams showing a second process of the semiconductor device 101 according to the second embodiment of the present invention.
Figure 19B:
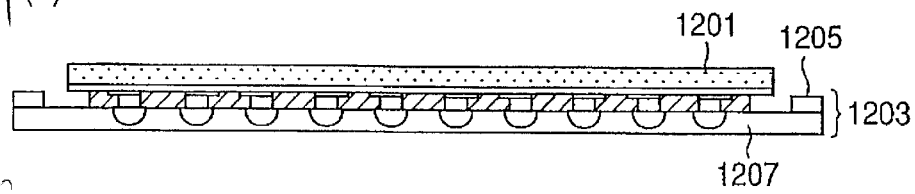
Figure 19C:
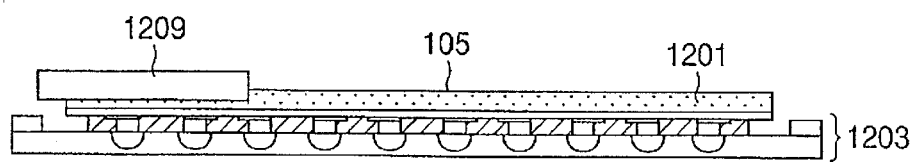

A second process employed in the present embodiment will next be explained below using FIG. 19. Incidentally, since a first process is identical to that employed in the first embodiment, the description thereof will be omitted. FIG. 19 is a process diagram showing the second process for the semiconductor device 101 according to the present embodiment. Since FIGS. 19(A) through 19(C) are identical to the first embodiment, the description thereof will be omitted.

Figure 19D:
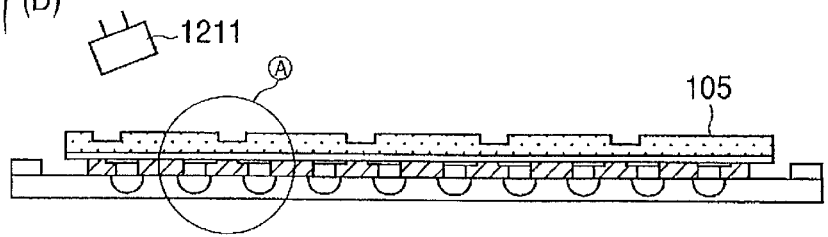
Figure 19E:
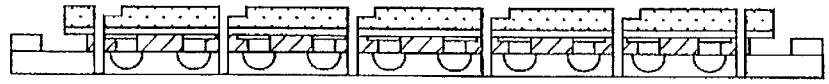

As shown in FIG. 19(D), a semiconductor wafer 1101 is placed on a dual dicing device with an unillustrated infrared camera 1211 in a state of being placed on a wafer ring 1203. The dual dicing device has two blades provided side by side. In the present embodiment, a first blade whose sectional shape is rectangular and whose thickness is 30 µm, and a second blade whose thickness is 150 µm, are used.

Figure 20:
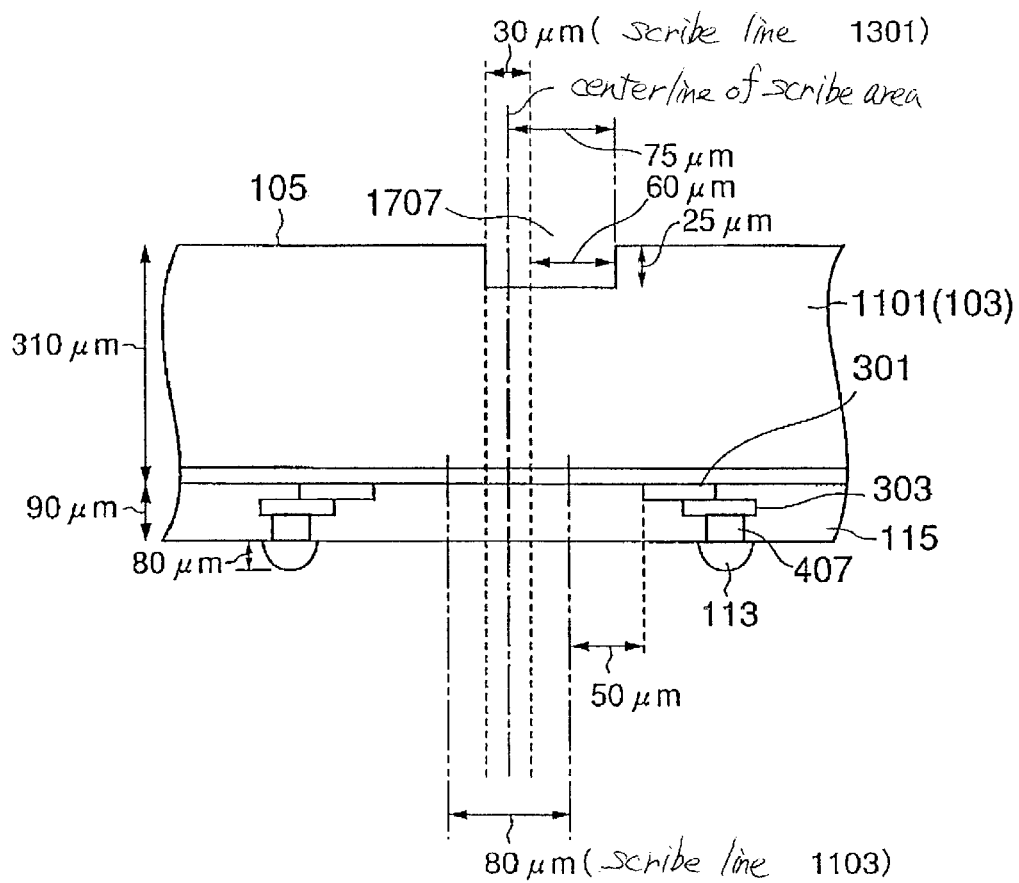
FIG. 20 is a diagram illustrating a schematic section of a portion indicated by a round mark "A" in a process step of FIG. 19(D).

FIG. 20 shows a schematic cross-section of a portion to which a round mark "A" in FIG. 19D) is affixed. The width of each scribe area 1103 is defined as about 80 µm. The distance between the edge of the scribe area 1103 and the edge of each electrode pad 301 is defined as about 50 µm. The width of each scribe line 1301 to be cut later is about 30 µm substantially identical to that of the first blade. Steplike sections 1707 formed in the process step of FIG. 19(D) are formed in a range of about 90 µm corresponding to the sum of about 75 µm to the right side and about 15 µm to the left side as viewed from the center line of each scribe area. In this stage, the width of each steplike section 1707 is about 150 µm identical to the width of the second blade, and the depth thereof is about 25 µm.

As shown in FIG. 19(D), pattern shapes of a plurality of electrode pads 301 or metal wiring layers 303 formed on the surface 109 side of the semiconductor wafer are first recognized from the back of the semiconductor wafer 1101 by means of the infrared camera 1211. Consequently, the scribe areas 1103, which exist on the surface 109 of the semiconductor wafer 1101, are recognized by the dicing device.

Figure 21:
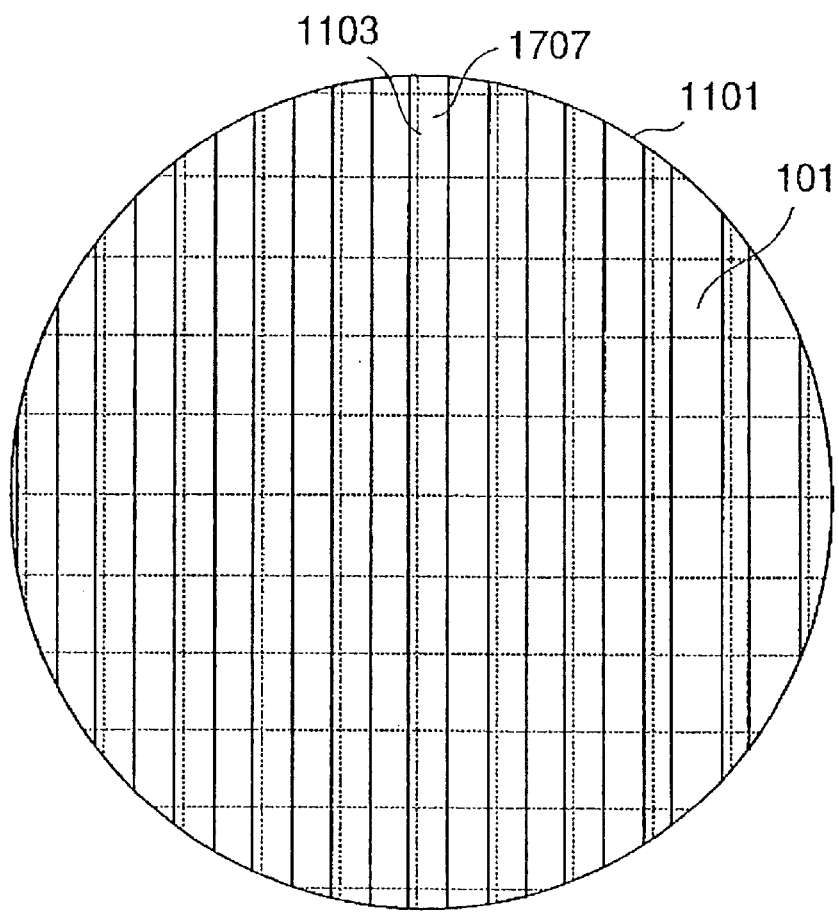
FIG. 21 is a diagram showing the reverse side of a semiconductor wafer 1101 in the process step of FIG. 19(D).

Next, the second blade is placed on the above-described range shown in FIG. 20 including the center line of each scribe area 1103. Thereafter, the back 105 of the semiconductor wafer 1101 is ground (half-cut) about 25 µm by the second blade so that each steplike portion 1707 is formed (see FIG. 20). The surface of the steplike portion 1707 is also coarser than the other back 105 of the semiconductor wafer 1101 (semiconductor substrate 103) held in the mirror state according to the grinding done by the second blade. The grinding by the second blade is executed in association with the respective semiconductor devices 101 of the semiconductor wafer 1101 (see FIG. 19(D)). FIG. 21 is a diagram showing the back side of the semiconductor wafer 1101 in the process step of FIG. 19(D). It can be understood that the steplike portion 1707 formed by the second blade is formed along one side of the respective semiconductor devices 101.

Next, the first blade is placed on the center line of each scribe area 1103, i.e., the scribe line 1301. Thereafter, the back 105 of the semiconductor wafer 1101 is ground (fully cut) about 400 µm along the scribe line 1301 by the first blade. The grinding by the first blade is executed in association with the respective semiconductor devices 101 of the semiconductor wafer 1101. As a result, the respective semiconductor devices 101 are brought into fractionalization (see FIG. 19(E)).

Next, the semiconductor wafer 1101 is shifted to an expand ring together with a dicing sheet 1207. Thereafter, the dicing sheet 1207 is subjected to ultraviolet rays, so that its adhesive power is reduced. The dicing sheet 1207 is extended in the outer peripheral direction of the semiconductor wafer 1101 and the respective semiconductor devices 101 are taken out by a collet.

The semiconductor device 101 shown in FIGS. 17 and 18 is finally obtained through the above-described second process.

According to the semiconductor device showing the second embodiment of the present invention, it has the following peculiar effects in addition to the effects obtained by the semiconductor device according to the first embodiment. Namely, since the steplike section 1707 is formed along the side face of the semiconductor substrate 121, no stress is concentrated on the steplike section 1707 even if bending stress is applied to the semiconductor device 101 mounted on the printed circuit board through the printed circuit board. Accordingly, the possibility that the semiconductor device 101 will break due to the above bending stress, can be reduced to the utmost. Further, since the steplike section 1707 is formed along the side face of the semiconductor substrate 103 on which no stress is concentrated, the area for the steplike section 1707 can be made wider as compared with the first embodiment. Thus, the accuracy of detection of the orientation of the semiconductor device visually or by an image recognizer can be expected to be further improved as compared with the first embodiment.

Figure 22:
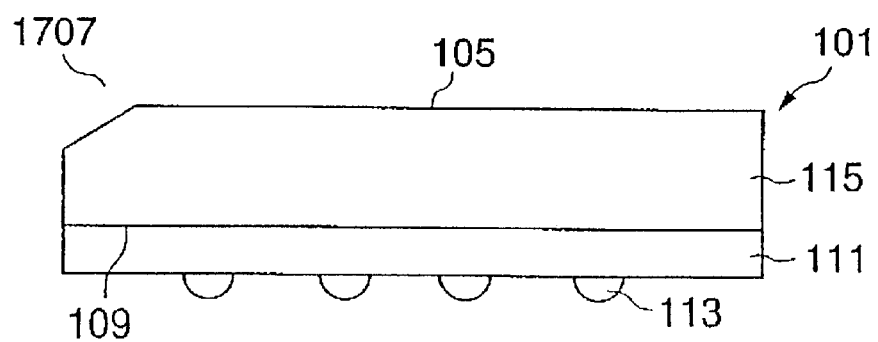
FIG. 22 is a diagram illustrating a modification of a semiconductor device according to the second embodiment of the present invention.

Incidentally, the steplike section 1707 according to the present invention may take such a shape as shown in FIG. 22, for example, i.e., an inclined or slope shape as well as such a shape as shown in FIGS. 17 and 18. In this case, the steplike section 1707 might as well be called a "slope section or portion 1707". In the specification of the present application, however, such an inclined or slope shape as shown in FIG. 22 is also described as a steplike shape (steplike section).

Figure 23:
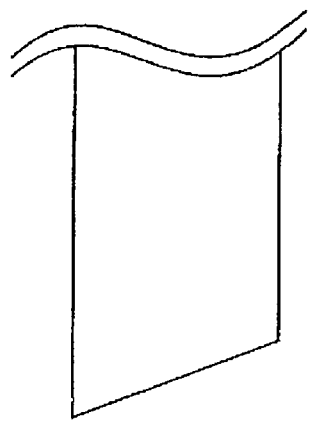
FIG. 23 is a cross-sectional view of a second blade used upon the fabrication of the modification of the semiconductor device according to the second embodiment of the present invention.

Incidentally, a second blade having such a sectional shape as shown in FIG. 23 is used to form such a slope section 1707 as shown in FIG. 22. In short, the steplike section 1707 or the inclined section 1707 may be formed along on side face of the semiconductor substrate 103.

Third Preferred Embodiment

A third embodiment of a semiconductor device according to the present invention will next be described below with reference to the accompanying drawings.

Figure 24:
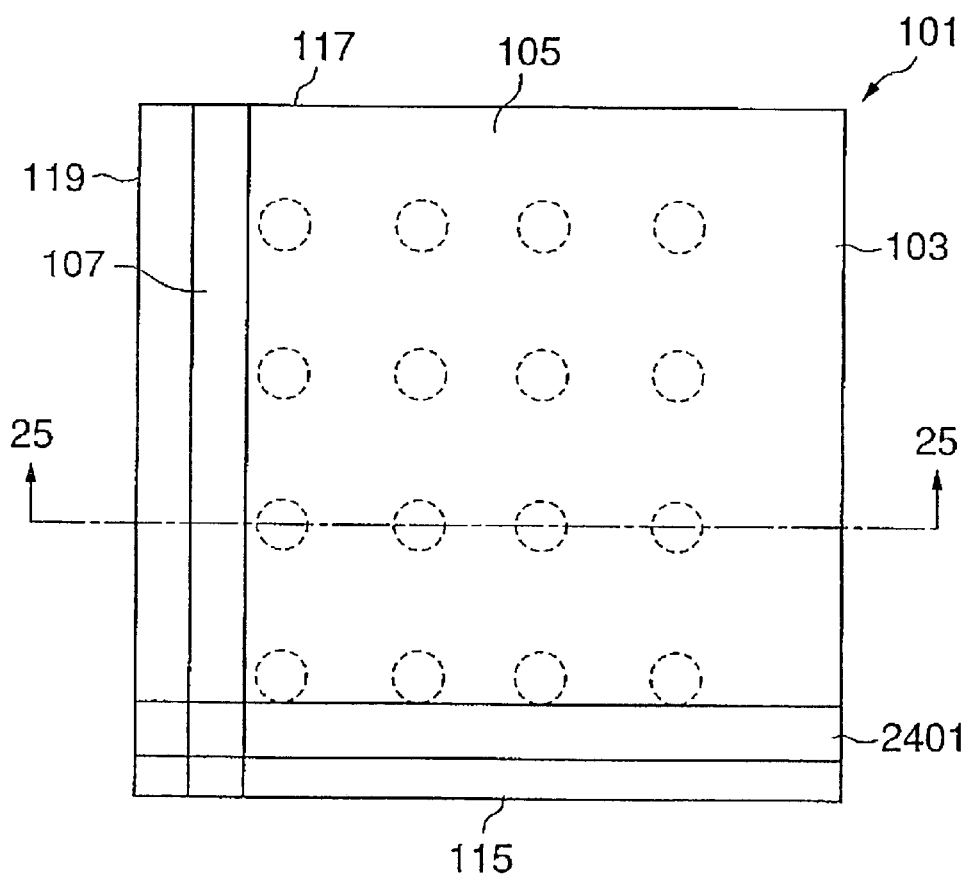
FIG. 24 is a plan perspective view showing the back of a semiconductor device 101 according to a third embodiment of the present invention.
Figure 25:
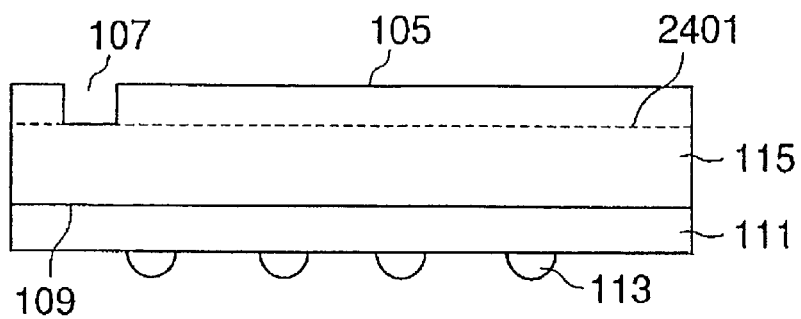
FIG. 25 is a schematic cross-sectional view taken along line 25—25 of FIG. 24.

FIG. 24 is a plan perspective view showing a third embodiment of a semiconductor device 101 according to the present invention, and FIG. 25 is a schematic cross-sectional view taken along line 25—25 of FIG. 24, respectively.

The third embodiment resides in that an additional steplike section 2401 is formed in a reverse side or back 105 in addition to the steplike section 107 employed in the first embodiment. Since the third embodiment is substantially similar to the first embodiment in other configurations, the detailed description thereof will be omitted.

As shown in FIGS. 24 and 25, a semiconductor substrate 103 has a steplike section 107 (also called a "concave portion, trench portion or slit") formed in a back 105, and the additional steplike section 2401. The additional steplike section 2401 is a portion added to the first embodiment. The steplike section 2401 is formed in the back 105 so as to extend from a third side face 119 of the semiconductor substrate 103 to a fourth side face opposite to the third side face 119. Further, the steplike section 2401 is formed in the back 105 lying in the neighborhood of a first side face 115.

Here, the term of "neighborhood of the first side face 115 at which the steplike section 2401 is formed" means a place located on the first side face 115 side as viewed from the center of the semiconductor substrate 103.

Figure 26:
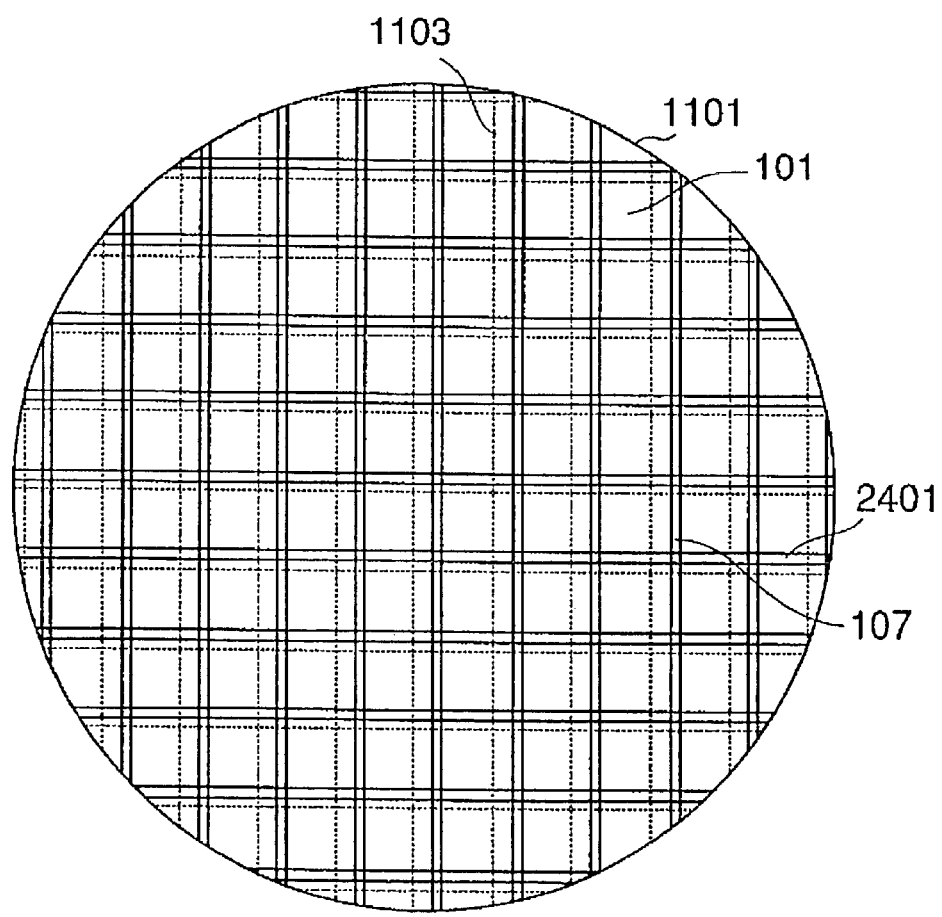
FIG. 26 is a diagram showing the reverse side of a semiconductor wafer 1101 used for semiconductor devices each showing the third embodiment of the present invention.

The additional steplike section 2401 can be formed by a second blade after the process step of FIG. 12(D) while the semiconductor wafer 1101 is being turned 90°. FIG. 26 is a diagram showing the back side of a semiconductor wafer 1101. It should be understood that the additional steplike sections 2401 formed by the second blade are formed along one sides of the respective semiconductor devices 101. Incidentally, since the above-described forming method can easily be understood by those skilled in the art, the detailed description thereof will be omitted.

According to the semiconductor device showing the third embodiment of the present invention, it has the following peculiar effects in addition to the effects obtained by the semiconductor device according to the first embodiment. Namely, since a point where the steplike section 107 and the steplike section 2401 intersect, can be utilized as one pin mark, the position of each first pin can accurately be recognized.

Incidentally, it will easily be estimated by those skilled in the art that even if the additional steplike section 2401 according to the present invention may be V-shaped or U-shaped.

Figure 27:
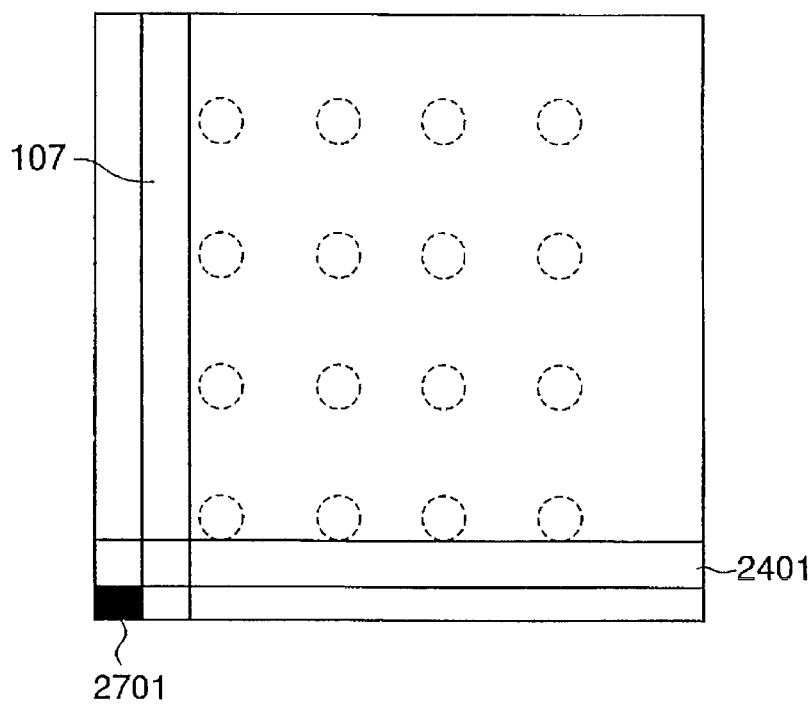
FIG. 27 is a diagram illustrating a modification of the semiconductor device according to the third embodiment of the present invention.

Further, a modification of the third embodiment is shown in FIG. 27. In present modification as shown in FIG. 27, an ink-based seal is placed on the narrowest area 2701 of areas comparted by four side faces of a steplike section 107, a steplike section 2401, and a semiconductor substrate 103.

According to the present modification, the position of each first pin can more accurately be recognized.

Fourth Preferred Embodiment

A fourth embodiment of a semiconductor device according to the present invention will next be described below with reference to the accompanying drawings.

Figure 28:
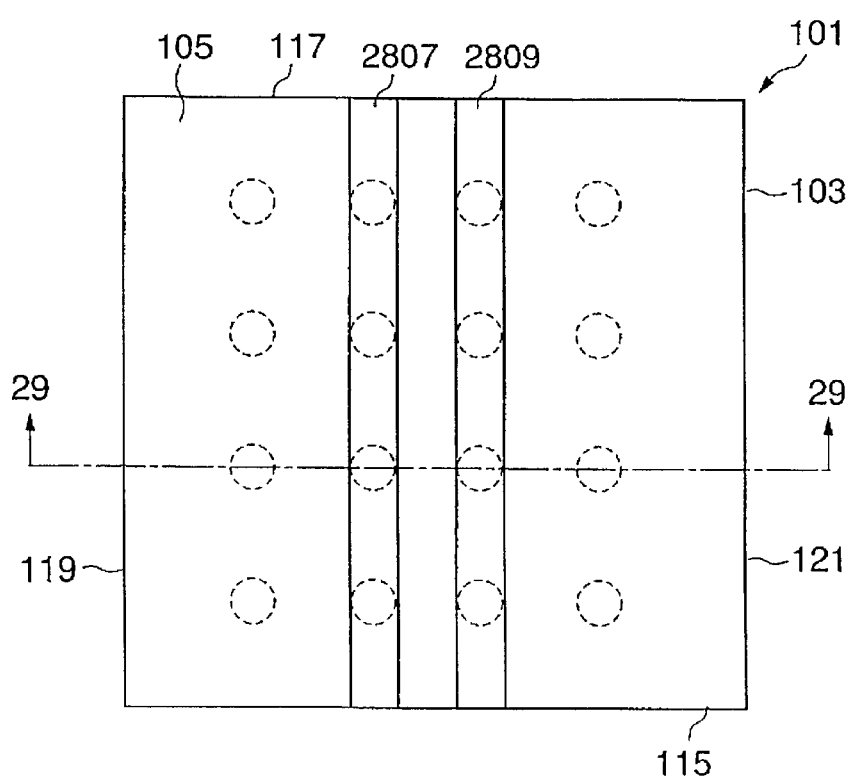
FIG. 28 is a plan perspective view showing a fourth embodiment of a semiconductor device 101 according to the present invention.
Figure 29:
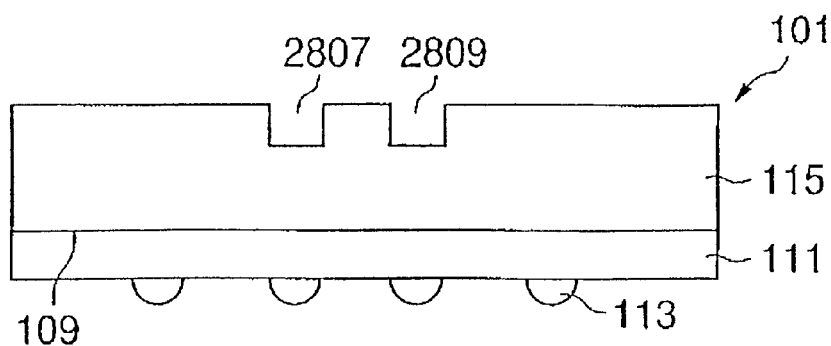
FIG. 29 is a schematic cross-sectional view taken along line 29—29 of FIG. 28.

FIG. 28 is a plan view showing the fourth embodiment of the semiconductor device 101 according to the present invention, and FIG. 29 is a schematic cross-sectional view taken along line 29—29 of FIG. 28, respectively.

The fourth embodiment resides in that a steplike section 2807 and a steplike section 2809 are formed in a back 105 in place of the steplike section 107 employed in the first embodiment. Since the fourth embodiment is substantially similar to the first embodiment in other configurations, the detailed description thereof will be omitted.

As shown in FIGS. 28 and 29, a semiconductor substrate 103 has the steplike section 2807 (also called "concave portion, trench portion or slit") formed in the back 105, and the steplike section 2809 formed therein. These steplike sections 2807 and 2809 are formed in the back 105 so as to extend from a first side face 115 of the semiconductor substrate 103 to a second side face 117 opposite to the first side 115. Further, the steplike section 2807 is provided within the back 105 of the semiconductor substrate 103 so as to correspond to a predetermined one row of a plurality of protruded electrodes 113 placed in matrix form. The steplike section 2809 is provided within the back 105 of the semiconductor substrate 103 so as to correspond to another one row of the plurality of protruded electrodes 113 arranged in matrix form.

Figure 30:
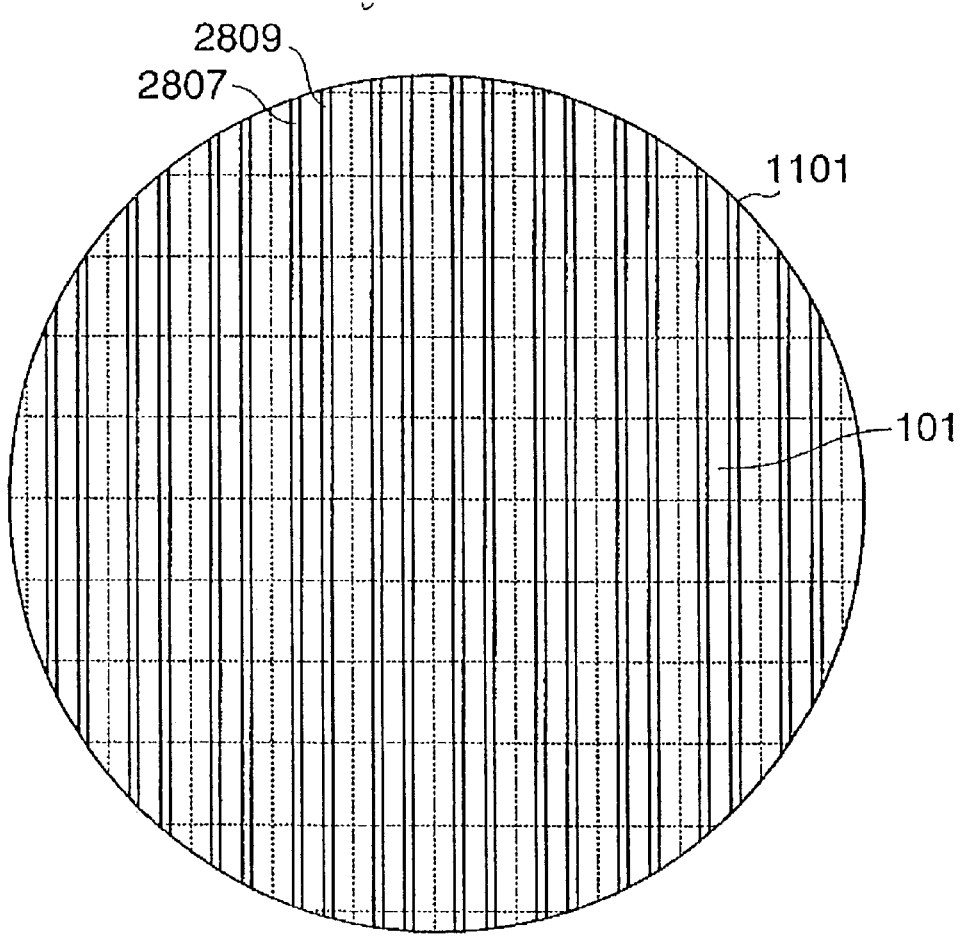
FIG. 30 is a diagram illustrating the back side of a semiconductor wafer 1101 used for semiconductor devices each showing the fourth embodiment of the present invention.

These steplike sections 2807 and 2809 can be formed by the second blade in the process step of FIG. 12(D). FIG. 30 is a diagram showing the back side of a semiconductor wafer 1101. It will be understood that the steplike sections 2807 and 2809 formed by the second blade are formed in association with the respective semiconductor devices 101. Incidentally, since the above-described forming method can easily be understood by those skilled in the art, the detained description thereof will be omitted.

According to the semiconductor device showing the fourth embodiment of the present invention has the following peculiar effects.

Namely, the position of each protruded electrode 113 can be recognized from the back 105 side of the semiconductor substrate 103. Thus, when the semiconductor device 101 is mounted on the printed circuit board 501 (see FIGS. 5 an 6), the alignment of the protruded electrodes 113 with the wirings 507 formed on the printed circuit board 501 can be realized with satisfactory accuracy. Detecting a displacement of each of the steplike sections 2807 and 2809 from the wiring 507 in a visual inspecting process makes it possible to easily inspect that the semiconductor device 101 has properly been placed on the printed circuit board 501.

Incidentally, it can easily be estimated by those skilled in the art that the steplike sections 2807 and 2809 according to the present invention may be V-shaped or U-shaped.

An advantageous effect obtained by a typical semiconductor device of the inventions disclosed in the present application will be described in brief as follows:

According to the semiconductor device of the present invention, since a steplike section (trench) is provided in a second main surface opposite to a first main surface on which circuit elements are formed, the orientation of mounting or packaging of the semiconductor device can easily be determined. Further, the above steplike section (trench) can be formed in the process of fractionalizing semiconductor devices. Thus, the above excellent semiconductor device can be manufactured without substantially adding a special process for forming the steplike section (trench).

While the preferred form of the present invention has been described, it is to be understood that modifications will be apparent to those skilled in the art without departing from the spirit of the invention. The scope of the invention is to be determined solely by the following claims.

What is claimed is:

1. A semiconductor device comprising:
   a semiconductor substrate having a first main surface having circuit elements formed thereon, a second main surface substantially opposite to the first main surface, and a plurality of side faces provided between the first main surface and the second main surface; and
   a plurality of external terminals formed over the first main surface and respectively electrically connected to the circuit elements,
   wherein the second main surface has a first steplike section which extends from a first side face of the plurality of side faces to a second side face opposite to the first side face, and
   wherein the second main surface is divided by the steplike section asymmetrically.

2. The semiconductor device according to claim 1, wherein the first steplike section is formed in the neighborhood of a third side face of the plurality of side faces, which is adjacent to the first and second side faces.

3. The semiconductor device according to claim 2, wherein the first steplike section has a cross-section formed in a substantially V shape.

4. The semiconductor device according to claim 2, wherein the first steplike section has a cross-section formed in a substantially U shape.

5. The semiconductor device according to claim 1, wherein the first steplike section is formed along the third side face of the plurality of side faces, which is adjacent to the first and second side faces.

6. The semiconductor device according to claim 5, wherein the thickness of the semiconductor substrate, in the first steplike section, becomes smaller approaching an outer edge of the semiconductor device.

7. The semiconductor device according to claim 1, wherein the second main surface has a second steplike section which extends from the third side face to a fourth side face of the plurality of side faces, which is opposite to the third side face.

8. The semiconductor device according to claim 1, wherein the external terminals comprise a plurality of external terminal groups disposed in plural rows, and the first steplike section is formed in the second main surface corresponding to a predetermined row of the plural rows.

9. The semiconductor device according to claim 1, wherein a sealing resin is disposed on the first main surface, and the external terminals are exposed from the surface of the sealing resin.

10. The semiconductor device according to claim 2, wherein a sealing resin is disposed on the first main surface, and the external terminals are exposed from the surface of the sealing resin.

11. The semiconductor device according to claim 3, wherein a sealing resin is disposed on the first main surface, and the external terminals are exposed from the surface of the sealing resin.

12. The semiconductor device according to claim 4, wherein a sealing resin is disposed on the first main surface, and the external terminals are exposed from the surface of the sealing resin.

13. The semiconductor device according to claim 5 wherein a sealing resin is disposed on the first main surface, and the external terminals are exposed from the surface of the sealing resin.

14. The semiconductor device according to claim 6, wherein a sealing resin is disposed on the first main surface, and the external terminals are exposed from the surface of the sealing resin.

15. The semiconductor device according to claim 7, wherein a sealing resin is disposed on the first main surface, and the external terminals are exposed from the surface of the sealing resin.

16. The semiconductor device according to claim 8, wherein a sealing resin is disposed on the first main surface, and the external terminals are exposed from the surface of the sealing resin.

17. A semiconductor device comprising:
   a semiconductor substrate having a first main surface having circuit elements formed thereon, a second main surface substantially opposite to the first main surface, and a plurality of side faces provided between the first main surface and the second main surface; and
   a plurality of external terminals formed over the first main surface and respectively electrically connected to the circuit elements,
   wherein the semiconductor substrate has a first portion in which the distance from the first main surface to the second main surface is a first distance, and a second portion in which the distance from the first main surface to the second main surface is a second distance shorter than the first distance between a first side face of the plurality of side faces and a second side face opposite to the first side face, and wherein the second main surface is divided by the second portion asymmetrically.

18. The semiconductor device according to claim 17 wherein the second portion is formed in the neighborhood of a third side face of the plurality of side faces, which is adjacent to the first and second side faces.

19. The semiconductor device according to claim 18 wherein the second portion has a cross-section formed in a substantially V shape.

20. The semiconductor device according to claim 18 wherein the second portion has a cross-section formed in a substantially U shape.

21. The semiconductor device according to claim 17, wherein the second portion is formed along the third side face of the plurality of side faces, which is adjacent to the first and second side faces.

22. The semiconductor device according to claim 21, wherein the thickness of the semiconductor substrate, in the second portion, becomes smaller approaching the outer edge of the semiconductor device.

23. The semiconductor device according to claim 17, wherein the semiconductor substrate further includes a third portion in which the distance from the first main surface to the second main surface is the second distance between the third side face and a fourth side face of the plurality of side faces, which is opposite to the third side face.

24. The semiconductor device according to claim 17, wherein the external terminals comprise a plurality of external terminal groups disposed in plural rows, and the first portion is formed so as to correspond to a predetermined row of the plural rows.

25. The semiconductor device according to claim 17, wherein a sealing resin is disposed on the first main surface, and the external terminals are exposed from the surface of the sealing resin.

26. The semiconductor device according to claim 18, wherein a sealing resin is disposed on the first main surface, and the external terminals are exposed from the surface of the sealing resin.

27. The semiconductor device according to claim 19, wherein a sealing resin is disposed on the first main surface, and the external terminals are exposed from the surface of the sealing resin.

28. The semiconductor device according to claim 20, wherein a sealing resin is disposed on the first main surface, and the external terminals are exposed from the surface of the sealing resin.

29. The semiconductor device according to claim 22, wherein a sealing resin is disposed on the first main surface, and the external terminals are exposed from the surface of the sealing resin.

30. The semiconductor device according to claim 23, wherein a sealing resin is disposed on the first main surface, and the external terminals are exposed from the surface of the sealing resin.

31. The semiconductor device according to claim 24, wherein a sealing resin is disposed on the first main surface, and the external terminals are exposed from the surface of the sealing resin.

32. A semiconductor device comprising:
a semiconductor substrate having a first main surface having circuit elements formed thereon, a second main surface substantially opposite to the first main surface, and a plurality of side faces provided between the first main surface and the second main surface; and a plurality of external terminals formed over the first main surface and respectively electrically connected to the circuit elements, wherein a steplike section extending from a first side face of the plurality of side faces to a second side face opposite to the first side face is formed in the second main surface, and the thickness of the semiconductor substrate is a first thickness at the second main surface excluding the steplike section and is a second thickness thinner than the first thickness at the steplike section, and wherein the second main surface is divided by the steplike section asymmetrically.

33. The semiconductor device according to claim 32, wherein the steplike section is formed in the neighborhood of a third side face of the plurality of side faces, which is adjacent to the first and second side faces.

34. The semiconductor device according to claim 32, wherein the steplike section is formed along the third side face of the plurality of side faces, which is adjacent to the first and second side faces.

35. The semiconductor device according to claim 34, wherein the thickness of the semiconductor substrate, in the steplike section, becomes smaller approaching the outer edge of the semiconductor device.

36. The semiconductor device according to claim 32, wherein a sealing resin is disposed on the first main surface, and the external terminals are exposed from the surface of the sealing resin.

37. The semiconductor device according to claim 33, wherein a sealing resin is disposed on the first main surface, and the external terminals are exposed from the surface of the sealing resin.

38. The semiconductor device according to claim 34, wherein a sealing resin is disposed on the first main surface, and the external terminals are exposed from the surface of the sealing resin.

39. The semiconductor device according to claim 35, wherein a sealing resin is disposed on the first main surface, and the external terminals are exposed from the surface of the sealing resin.

40. A semiconductor device comprising:
a semiconductor substrate having a first main surface having circuit elements formed thereon, a second main surface substantially opposite to the first main surface, and a plurality of side faces provided between the first main surface and the second main surface; and a plurality of external terminals formed over the first main surface and respectively electrically connected to the circuit elements, wherein the second main surface has a first portion which extends from a first side face of the plurality of side faces to a second side face opposite to the first side face and whose roughness is coarser than that of the second main surface excluding the first portion, and wherein the second main surface is divided by the first portion asymmetrically.

41. The semiconductor device according to claim 40, wherein the first portion is formed in the neighborhood of a third side face of the plurality of side faces, which is adjacent to the first and second side faces.

42. The semiconductor device according to claim 41, wherein the first portion has a cross-section formed in a substantially V shape.

43. The semiconductor device according to claim 41, wherein the first portion has a cross-section formed in a substantially U shape.

44. The semiconductor device according to claim 40, wherein the first portion is formed along the third side face of the plurality of side faces, which is adjacent to the first and second side faces.

45. The semiconductor device according to claim 44, wherein the thickness of the semiconductor substrate, in the first portion, becomes smaller approaching the outer edge of the semiconductor device.

46. The semiconductor device according to claim 40, wherein the second main surface has a second portion which extends from the third side face to a fourth side face opposite to the third side face, of the plurality of side faces and whose roughness is coarser than that of the second main surface excluding the first and second portions.

47. The semiconductor device according to claim 40, wherein the external terminals comprise a plurality of external terminal groups disposed in plural rows, and the first portion is formed in the second main surface corresponding to a predetermined row of the plural rows.

48. The semiconductor device according to claim 40, wherein a sealing resin is disposed on the first main surface, and the external terminals are exposed from the surface of the sealing resin.

49. The semiconductor device according to claim 41, wherein a sealing resin is disposed on the first main surface, and the external terminals are exposed from the surface of the sealing resin.

50. The semiconductor device according to claim 42, wherein a sealing resin is disposed on the first main surface, and the external terminals are exposed from the surface of the sealing resin.

51. The semiconductor device according to claim 43, wherein a sealing resin is disposed on the first main surface, and the external terminals are exposed from the surface of the sealing resin.

52. The semiconductor device according to claim 44, wherein a sealing resin is disposed on the first main surface, and the external terminals are exposed from the surface of the sealing resin.

53. The semiconductor device according to claim 45, wherein a sealing resin is disposed on the first main surface, and the external terminals are exposed from the surface of the sealing resin.

54. The semiconductor device according to claim 46, wherein a sealing resin is disposed on the first main surface, and the external terminals are exposed from the surface of the sealing resin.

55. The semiconductor device according to claim 47, wherein a sealing resin is disposed on the first main surface, and the external terminals are exposed from the surface of the sealing resin.

* * * * *